US006566330B1

(12) United States Patent
Dix

(10) Patent No.: US 6,566,330 B1
(45) Date of Patent: May 20, 2003

(54) POSITIVELY CHARGED NON-NATURAL AMINO ACIDS, METHODS OF MAKING AND USING THEREOF IN PEPTIDES

(75) Inventor: Thomas A. Dix, Mt. Pleasant, SC (US)

(73) Assignee: Medical University of South Carolina Foundation Research Development, Charleston, SC (US)

(*) Notice: Subject to any disclaimer, the term of this patent is extended or adjusted under 35 U.S.C. 154(b) by 0 days.

(21) Appl. No.: 09/659,665

(22) Filed: Sep. 11, 2000

Related U.S. Application Data

(60) Continuation-in-part of application No. 09/452,575, filed on Dec. 1, 1999, which is a division of application No. 08/736,049, filed on Oct. 22, 1996, now Pat. No. 6,043,218.

(51) Int. Cl.[7] .............................................. A61K 38/00
(52) U.S. Cl. ............................ 514/12; 514/13; 514/14; 514/15; 514/16; 514/17; 514/18; 514/19; 514/20; 548/327.5; 436/86; 530/324; 530/325; 530/326; 530/327; 530/328; 530/329; 530/330; 530/331
(58) Field of Search .................... 548/327.5; 436/86; 530/324–331; 514/12–20

(56) References Cited

U.S. PATENT DOCUMENTS

| | | |
|---|---|---|
| 3,178,472 A | 4/1965 | Hellerbach et al. |
| 3,303,213 A | 2/1967 | Kalopissis et al. |
| 4,061,542 A | 12/1977 | Demny et al. |
| 4,801,577 A | 1/1989 | Nestor, Jr. et al. |
| 5,407,916 A | 4/1995 | Wise et al. |
| 5,494,898 A | 2/1996 | Cheng et al. |
| 5,863,931 A | 1/1999 | Beams et al. |
| 6,127,420 A | 10/2000 | Griffith et al. |

FOREIGN PATENT DOCUMENTS

| | | |
|---|---|---|
| DE | 3327873 A1 | 2/1984 |
| DE | 19933701 A1 | 1/2001 |
| EP | 0145258 A1 | 6/1985 |
| EP | 0326766 A1 | 8/1989 |
| EP | 0472220 A1 | 2/1992 |
| EP | 0498941 A2 | 8/1992 |
| WO | WO 89/01944 | 3/1989 |
| WO | WO 93/13055 | 7/1993 |
| WO | WO 94/25477 | 11/1994 |
| WO | WO 94/28921 | 12/1994 |
| WO | WO 98/17626 | 4/1998 |
| WO | WO 98/48826 | 11/1998 |

OTHER PUBLICATIONS

Harper's Review of Biochemistry pp. 18–19 (1985).*

Richelson et al., "Novel Potent Neurotensin (8–13) mimetics." Abstracts of Papers of the ACS 215: 148–Medi, Part 1, Apr. 2, 1998.

Richelson et al., "Synthesis of a Potent Wide–spectrum Serotonin–, Norepnepherine– Dopamine–reuptake Inhibitor (SNDRI) and a Species–specific Dopamine–reuptake Inhibitor Based on the Gamma–amino Alcohol Functional Group." Abstracts of Papers of the ACS 215: 154–Medi, Part 1, Apr. 2, 1998.

Richelson et al., "Development of Nonpeptidic Neurotensin (8–13) Mimetics." Abstracts of Papers of the ACS 213: 61–Medi, Part 1, Apr. 13, 1998.

Richelson et al., "Development of a Neurotensin Agonist Crossing the Blood Brain Barrier," Biol. Psychiatry 43, 49S, 1998.

Lindeberg, et al, Solid Phase Synthesis And Some Hormonal Activities of 1–Deamino–4–L–Valine–8–D–Homolysine– And 1–Deamino–4–L–Valine–8–D–Homoarginine–Vasapressin, Int. J. Peptide Protein Res. 10, 240–244, 1977.

Moore, et al., Effect of the basic amino–acid side chain length and the penultimate residue on the hydrolysis of benzoyldipeptides by carboxypeptidbase B[1], Can. J. Biochem, 56, 315–318, 1978.

Nestor, et al., Potent, Long–Acting Luteinizing Hormone–Releasing Hormone Antagonists Containing New Synthetic Amino Acids: N,N'–Dialkyl–D–homoarginines[1], J. Med. Chem, 31, 65–72, 1988.

Hilbert, et al., Design and Synthesis of Potent and Highly Selective Thrombin Inhibitors, J. Med. Chem. 37, 3889–3901, 1994.

U.S. patent application Ser. No. 10/043,581, Dix, filed Jan. 10, 2002.

Chebotareva et al. Lipoic Acid (6,8–Dithiooctanic Acid)— (II) Synthesis of Benzhydrylammonium Salts of DL–, α.–Lipoyl–L–Phenylalanine, –L–Methionine, and –L–Valine. *Chemical Abstracts Service*, Database Accession No. CA62:7859a/AN, CAOLD, XP002194817, 62(7) (1965).

Havinga and Schattenkerk. Studies on Polypeptides—V[1]: Properties of the Arginyl Residue of Des–Asp[1]–Ile[5]–Angiotensin II Essential to Pressor Activity. *Tetrahedron*, 8(Part I):313–319 (1966).

Hempel and Lange. Synthese Tritium–markierter, N–methylierter Lysine. *Hoppe–Seyler's Z. Physiol. Chem.*, 350:867–876 (1969).

(List continued on next page.)

*Primary Examiner*—Sheela Huff
(74) *Attorney, Agent, or Firm*—Needle & Rosenberg, P.C.

(57) ABSTRACT

This invention relates to positively charged non-natural amino acids, methods of making thereof, and utilization thereof in peptides.

21 Claims, 2 Drawing Sheets

OTHER PUBLICATIONS

Takahara et al. $N^\omega$–Dimethyl– or $N^\omega$–trimethyl–2, $^\omega$–diaminocarboxylic acids. *6001 Chemical Abstracts*, XP002194816, 69(25) (1968).

Kennedy et al. Asymmetric Synthesis of Non–Natural Homologues of Lysine. *Bioorganic & Medical Chem. Ltrs.*, 7(14):1937–1940 (1997).

Kennedy et al. Design rationale, synthesis, and characterization of non–natural analogs of the cationic amino acids arginine and lysine. *J. Peptide Res.*, 55(4):348–358 (2000).

Lundquist and Dix. Synthesis and Human Neurotensin Receptor Binding Activities of Neurotensin(8–13) Analogues Containing Position 8 α–Azido–N–alkylated Derivatives of Ornithine, Lysine, and Homolysine. *J. Med. Chem.*, 42:4914–4918 (1999).

Moore et al. $N^\epsilon,N^\epsilon$–Dimethyl–lysine cytochrome c as an NMR probe for lysine involvement in protein–protein complex formation. *Biochem. J.*, 332:439–449 (1998).

Porcelli et al. A Kinetic Analysis of γ–Aminobutyrate Aminotransferase in Presence and Absence of Inhibitors. *Ber. Bunsenges. Phys. Chem.*, 100(5):671–679 (1996).

Takemoto et al. Hypotensive Constitutents of Marine Algae—(I) Basic Amino Acid, Laminine, and the Basic Constituents Isolated from Laminaria Augustata (II) Synthesis of Laminine and Related Compounds, *Chemical Abstracts Service*, Database Accession No. CA62:785e/AN, CAOLD, XP002194818, 84(12):1176–1182 (1964).

Tsuzuki et al. Synthesis of [$^2H_9$]– and [$^2H_6$]–Lysines. *J. Chem. Res.*, S:412–413 (1996).

Lindquist et al. Synthesis of Ethylene–Bridged (N ← to Nω) Analogues of Arginine, *J. Org. Chem.* 64:9265–9267 (Nov. 20, 1999), XP–002207133.

Folk et al. Carboxypeptidase B, *J. Biol. Chem.* 231:379–391 (1958), XP–001040454 (Abstract).

Lee et al. Solid–Phase Syntheses of $N^\omega$–Pyropylargginie–Containing Dipeptides, Dipeptides, Dipeptide Esters, and Dipeptide Amides, *Synthesis* SI:1495–1499 (1999), XP–002207134.

Nester et al. Potent Gonadotropin Releasing Hormone Antagonists with Low Histamine–Releasing Activity, *J. Med. Chem.* 35:3942–3948 (1992), XP–001074059.

* cited by examiner

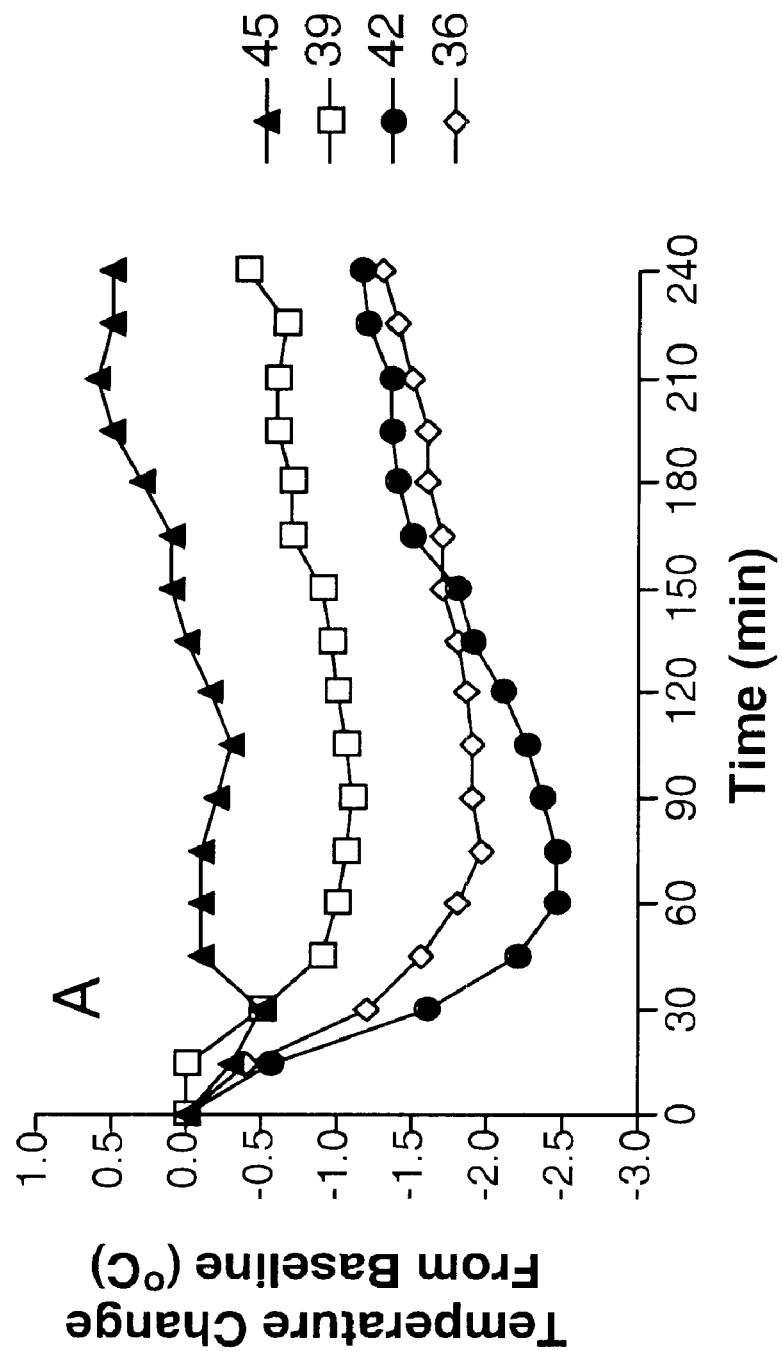

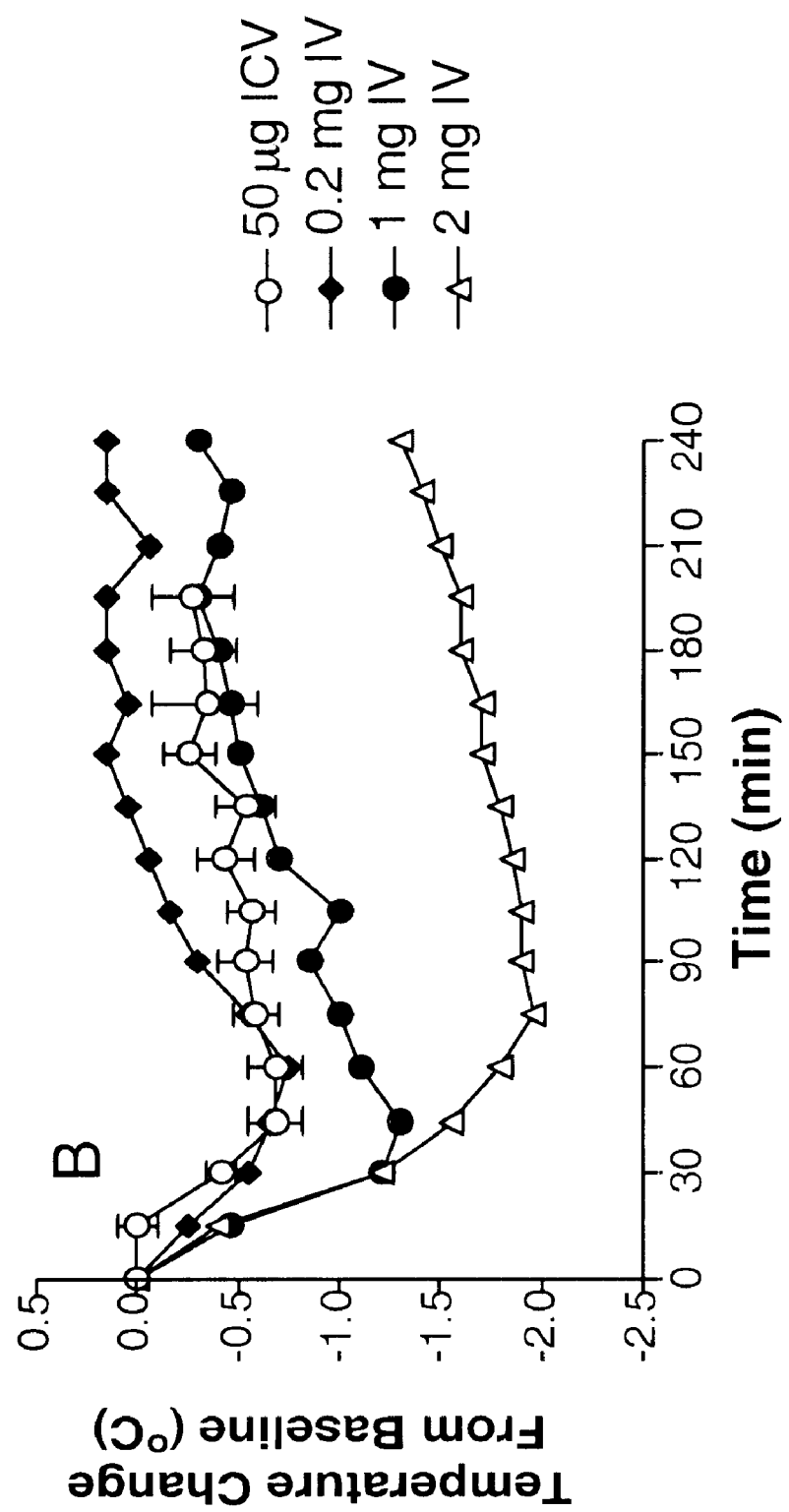

POSITIVELY CHARGED NON-NATURAL AMINO ACIDS, METHODS OF MAKING AND USING THEREOF IN PEPTIDES

CROSS REFERENCE TO RELATED APPLICATIONS

This application is a continuation-in-part of U.S. application Ser. No. 09/452,575, filed Dec. 1, 1999, pending, which is a divisional application of Ser. No. 08/736,049, filed on Oct. 22, 1996, which is U.S. Pat. No. 6,043,218, issued on Mar. 28, 2000. Each application and patent are hereby incorporated by this reference in their entireties for all of their teachings.

BACKGROUND OF THE INVENTION

1. Field of the Invention

This invention relates to positively charged non-natural amino acids, methods of making them and their utilization in peptides.

2. Background

Synthetic studies have been directed toward understanding the influence that only some non-natural amino acids have on the structural and biological activity of peptides.

U.S. Pat. No. 3,178,472 to Hellerbach et al. discloses a method for the conversion of amino carboxylic acids to their N-monomethyl derivatives. Naturally occurring amino acids such as alanine, phenylalanine, serine, cysteine, cystine, tyrosine, tryptophan, histidine, methionine, valine, norvaline, leucine, isoleucine, arginine, ornithine, lysine, aspartic acid, glutaminic acid, threonine, $\alpha,\gamma$-diaminobutyric acid and the like are suitable starting materials. When the starting material aminocarboxylic acid contains two amino groups such as lysine, ornithine or $\alpha,\gamma$-diaminiobutyric acid, then it is possible to generate a product in which one or both amino groups are methylated.

Moore et al. (*Can. J. Biochem.* 1978, 56, 315) discloses the effect of the basic amino acid side chain length and the penultimate residue on the hydrolysis of benzoyldipeptides by carboxylicpeptidase $B^1$ (CPB). Non-natural amino acids including homolysine and homoarginine were incorporated into small peptide chains, and the kinetic parameters were determined for the CPB catalyzed hydrolysis of the peptide.

Lindeberg et al. (*Int. J. Peptide Protein Res.* 1977, 10, 240) discloses the synthesis of 1-deamino-4-L-valine-8-DL-homolysine-vasopressin and protected 1-deamino-4-L-valine-8-D-lysine-vassopressin in which with non-natural amino acids were incorporated. The addition of a methylene group to lysine and arginine to generate the non-natural amino acids homolysine and homoarginine, respectively. The study revealed that peptides with homolysine and homoarginine reduced the antidiuretic activity of the peptides.

Hilpert et al. (*J. Med. Chem.* 1994, 37, 3889) discloses screening of small basic molecules for binding in the recognition pocket of thrombin led to the discovery of the arginine mimetic (aminoiminomethyl)piperidine as a weak thrombin inhibitor. A number of derivatives of the arginine mimetic were prepared, and their ability to inhibit thrombin was assayed. The X-ray crystal structure analysis of thrombin as well as modeling studies of the arginine mimetic were conducted in order to rationalize the observed affinity between the unnatural amino acid and thrombin.

Nestor et al. (*J. Med. Chem.* 1988, 31, 65) discloses the synthesis of a new series of unnatural amino acids and their incorporation into antagonistic analogues of lutenizing hormone-releasing hormone (LH-RH). In particular, non-natural amino acids of arginine exhibited high acute potency and very prolonged duration of action. Biological and clinical pharmacology studies revealed that these LH-RH antagonists cause mast cell degranulation, and were removed from consideration as candidates for full commercial development.

There is a need in the art for non-natural amino acids and for peptides incorporating such acids to achieve superior effects, such as, for example, improved diagnostic or disease fighting activity. None of the above references discloses the non-natural amino acids of the present invention or the advantageous properties thereof. The present invention accordingly describes positively charged non-natural amino acids, methods of making them and their utilization in peptides.

Additional advantages of the invention will be set forth in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIG. 1 shows the results of in vivo studies that demonstrate the ability of NT(8–13) derivatives to cause a central hypothermic effect after intravenous (I.V.) administration, indicating translocation across the BBB (A) hypothermia induced by 1.0 mg doses of peptides 36, 39, 42, and 45; (B) dose-dependent hypothermia observed for peptide 36 after I.V. administration with an estimated 28% brain uptake of the 0.2-mg I.V. dose as compared to intracranial (I.C.) administration.

DESCRIPTION OF THE PREFERRED EMBODIMENTS

The present invention may be understood more readily by reference to the following detailed description of preferred embodiments of the invention and the Examples included therein.

Before the present compounds, compositions and methods are disclosed and described, it is to be understood that this invention is not limited to specific synthetic methods, as such may, of course, vary. It is also to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains.

Variables, such as $R_1$–$R_{13}$, $R_{15}$, n, z, X, Y, $C_\alpha$ and $C_\beta$, throughout the application are the same variables as previously defined unless stated to the contrary.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Preferred alkyl groups herein contain from 1 to 5 carbon atoms.

The term "alkenyl" as used herein refers to a hydrocarbon group of 2 to 24 carbon atoms, with preferred groups within this class contain 2 to 5 carbon atoms, and structural formula containing a carbon-carbon double bond.

The term "alkynyl" as used herein refers to a hydrocarbon group of 2 to 24 carbon atoms, with preferred groups within this class containing 2 to 5 carbon atoms, and a structural formula containing a carbon-carbon triple bond.

As used herein, especially in reference to alkyl, alkenyl and alkynyl, unless defined otherwise, the term "lower" refers to a moiety having from 1 to 6 carbon atoms, preferably 1 to 4 carbon atoms, more preferably 1 to 2 carbon atoms.

The term "alkylating agent" as provided herein is a compound with the structural formula RX, where R is an alkyl, alkenyl or alkynyl group as previously described, and X, which is preferably a halide such as chloride, bromide or iodide.

As used herein, the term "non-natural amino acid" refers to an organic compound that has a structure similar to a natural amino acid so that it mimics the structure and reactivity of a natural amino acid. The non-natural amino acid as defined herein generally increases or enhances the properties of a peptide (e.g., selectivity, stability) when the non-natural amino acid is either substituted for a natural amino acid or incorporated into a peptide.

As used herein, the term "peptide" refers to a class of compounds composed of amino acids chemically bound together. In general, the amino acids are chemically bound together via amide linkages (CONH); however, the amino acids may be bound together by other chemical bonds known in the art. For example, the amino acids may be bound by amine linkages. Peptide as used herein includes oligomers of amino acids and small and large peptides, including polypeptides.

As used herein, the term "activity" refers to a biological activity.

As used herein, the term "pharmacological activity" refers to the inherent physical properties of a peptide or polypeptide. These properties include but are not limited to half-life, solubility, and stability and other pharmacokinetic properties.

The invention, in one aspect, relates to a non-natural amino acid compound of the formula I:

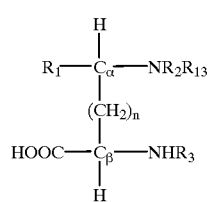

(I)

wherein
n is an integer of from 2 to 4;
$R_1$, $R_2$, $R_3$ and $R_{13}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

or the ester or salt thereof, wherein when $R_1$, $R_2$, $R_3$ and $R_{13}$ are all hydrogen, then n is not 2 or 3, when n is 2 or 3, $R_1$ and $R_{13}$ are hydrogen, and $R_2$ and $R_3$ are independently hydrogen or methyl with at least one of $R_2$ and $R_3$ being methyl, then the stereochemistry at $C_\beta$ is not S, and when n is 4, and $R_1$, $R_2$, $R_3$ and $R_{13}$ are all hydrogen, then the stereo chemistry at $C_\beta$ is not R.

In one embodiment, $R_1$, $R_2$, $R_3$ and $R_{13}$ are independently, hydrogen or lower branched or straight chain alkyl of $C_1$–$C_5$, preferably hydrogen or methyl. In another embodiment, n is 4. In one embodiment, the compound is:

a) n is 4, $R_1$, $R_3$ and $R_{13}$ are hydrogen, $R_2$ is methyl, the compound of formula I is an acid, and the stereochemistry at $C_\beta$ is R;

b) n is 4, $R_1$, $R_3$ and $R_{13}$ are hydrogen, $R_2$ is methyl, the compound of formula I is an acid, and the stereochemistry at $C_\beta$ is S;

c) n is 4, $R_1$ and $R_2$ are methyl, $R_3$ and $R_{13}$ are hydrogen, the compound of formula I is an acid, the stereochemistry at $C_\alpha$ is R, and the stereochemistry at $C_\beta$ is R;

d) n is 4, $R_1$ and $R_2$ are methyl, $R_3$ and $R_{13}$ are hydrogen, the compound of formula I is an acid, the stereochemistry at $C_\alpha$ is S, and the stereochemistry at $C_\beta$ is R;

e) n is 4, $R_1$ and $R_2$ are methyl, $R_3$ and $R_{13}$ are hydrogen, the compound of formula I is an acid, the stereochemistry at $C_\alpha$, is R, and the stereochemistry at $C_\beta$ is S;

f) n is 4, $R_1$ and $R_2$ are methyl, $R_3$ and $R_{13}$ is hydrogen, the compound of formula I is an acid, the stereochemistry at $C_\alpha$ is S, and the stereochemistry at $C_\beta$ is S;

g) n is 4, $R_1$ is methyl, $R_2$, $R_3$ and $R_{13}$ are hydrogen, the compound of formula I is an acid, the stereochemistry at $C_\alpha$ is R, and the stereochemistry at $C_\beta$ is R;

h) n is 4, $R_1$ is methyl, $R_2$, $R_3$ and $R_{13}$ are hydrogen, the compound of formula I is an acid, the stereochemistry at $C_\alpha$ is S, and the stereochemistry at $C_\beta$ is R;

i) n is 4, $R_1$ is methyl, $R_2$, $R_3$ and $R_{13}$ are hydrogen, the compound of formula I is an acid, the stereochemistry at $C_\alpha$ is R, and the stereochemistry at $C_\beta$ is S;

j) n is 4, $R_1$ is methyl, $R_2$, $R_3$ and $R_{13}$ are hydrogen, the compound of formula I is an acid, the stereochemistry at $C_\alpha$ is S, and the stereochemistry at $C_\beta$ is S;

k) n is 4, $R_1$, $R_2$, $R_3$ and $R_{13}$ are hydrogen, the compound of formula I is an acid, and the stereochemistry at $C_\beta$ is S;

l) n is 3, $R_1$ and $R_2$ are methyl, $R_3$ and $R_{13}$ are hydrogen, the compound of formula I is an acid, the stereochemistry at $C_\alpha$ is R, and the stereochemistry at $C_\beta$ is R;

m) n is 3, $R_1$ and $R_2$ are ethyl, $R_3$ and $R_{13}$ are hydrogen, the compound of formula I is an acid, the stereochemistry at $C_\alpha$ is S, and the stereochemistry at $C_\beta$ is R;

n) n is 3, $R_1$ and $R_2$ are propyl, $R_3$ and $R_{13}$ are hydrogen the compound of formula I is an acid, the stereochemistry at $C_\alpha$ is R, and the stereochemistry at $C_\beta$ is S;

o) n is 3, $R_1$ and $R_2$ are butyl, $R_3$ and $R_{13}$ is hydrogen, the compound of formula I is an acid, the stereochemistry at $C_\alpha$ is S, and the stereochemistry at $C_\beta$ is S;

p) n is 2, $R_1$ and $R_2$ are methyl, $R_3$ and $R_{13}$ are hydrogen, the compound of formula I is an acid, the stereochemistry at $C_\alpha$ is R, and the stereochemistry at $C_\beta$ is R;

q) n is 2, $R_1$ and $R_2$ are ethyl, $R_3$ and $R_{13}$ are hydrogen, the compound of formula I is an acid, the stereochemistry at $C_\alpha$ is S, and the stereochemistry at $C_\beta$ is R;

r) n is 2, $R_1$ and $R_2$ are propyl, $R_3$ and $R_{13}$ are hydrogen, the compound of formula I is an acid, the stereochemistry at $C_\alpha$ is R, and the stereochemistry at $C_\beta$ is S;

s) n is 2, $R_1$ and $R_2$ are butyl, $R_3$ and $R_{13}$ is hydrogen, the compound of formula I is an acid, the stereochemistry at $C_\alpha$ is S, and the stereochemistry at $C_\beta$ is S;

or the ester or salt thereof.

Preferably, the compound is one of the species a–k above.

The invention further relates to a non-natural amino acid compound of the formula II:

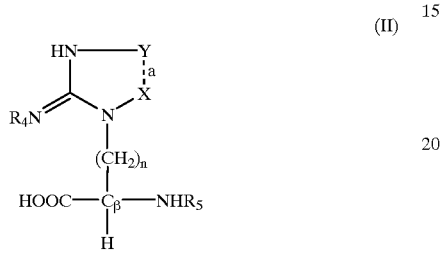

(II)

wherein n is an integer of from 2 to 4;

when dashed line a is not present, X and Y are independently, hydrogen or lower branched or straight chain alkyl, alkenyl or alkynyl of $C_1$–$C_5$;

when dashed line a is present, X–Y is $(CH_2)_z$, wherein z is an integer of from 2 to 4;

$R_4$ and $R_5$ are, independently, hydrogen or lower branched or straight chain alkyl, alkenyl or alkynyl of $C_1$–$C_5$; and $C_\beta$ is a carbon atom and the stereochemistry at $C_\beta$ is either R or S;

or the ester or salt thereof, wherein when n is 3, dashed line a is not present, $R_4$, X and Y are all hydrogen, and $R_5$ is methyl, then $C_\beta$ is not S, when n is 3, dashed line a is not present, X and $R_5$ are hydrogen, and Y and $R_4$ are methyl, then the stereochemistry at $C_\beta$ is not R, when dashed line a is not present, and $R_4$, $R_5$, X and Y are all hydrogen, then n is not 3, when n is 4, dashed line a is not present, X and $R_5$ are hydrogen, and Y and $R_4$ are the same lower branched or straight chain alkyl, then $C_\beta$ is not R, and when n is 4, dashed line a is not present, and $R_4$, $R_5$, X and Y are all hydrogen, then the stereochemistry at $C_\beta$ is not R.

In one embodiment, when n is 3, dashed line a is not present, X and $R_5$ are hydrogen, and Y and $R_4$ are the same lower branched or straight chain alkyl, then $C_\beta$ is not R. In a another embodiment, $R_4$ and $R_5$ are, independently, hydrogen or methyl. In a preferred embodiment, dashed line a is not present, X is hydrogen or lower branched or straight chain alkyl of $C_1$–$C_5$, preferably methyl or ethyl, and Y is hydrogen or lower branched or straight chain alkyl of $C_1$–$C_5$, preferably methyl, or dashed line a is present and z is 2, preferably, n is 3. In one embodiment, the compound is:

a) n is 3, dashed line a is not present, the compound of formula II is an acid, $R_4$ and R, are hydrogen, X is hydrogen, Y is methyl, and the stereochemistry at $C_\beta$ is R;

b) n is 3, dashed line a is not present, the compound of formula II is an acid, $R_4$ and $R_5$ are hydrogen, X is hydrogen, Y is methyl, and the stereochemistry at $C_\beta$ is S;

c) n is 3, dashed line a is not present, the compound of formula II is an acid, $R_4$ is methyl, $R_5$ is hydrogen, X is hydrogen, Y is methyl, and the stereochemistry at $C_\beta$ is S;

d) n is 3, dashed line a is present, the compound of formula II is an acid, z is 2, $R_4$ and $R_5$ are hydrogen, and the stereochemistry at $C_\beta$ is R;

e) n is 3, dashed line a is present, the compound of formula II is an acid, z is 2, $R_4$ and $R_5$ are hydrogen, and the stereochemistry at $C_\beta$ is S;

f) n is 3, dashed line a is present, the compound of formula II is an acid, z is 2, $R_4$ is methyl, $R_5$ is hydrogen, and the stereochemistry at $C_\beta$ is R;

g) n is 3, dashed line a is present, the compound of formula II is an acid, z is 2, $R_4$ is methyl, $R_5$ is hydrogen, and the stereochemistry at $C_\beta$ is S;

h) n is 3, dashed line a is not present, the compound of formula II is an acid, $R_4$ and $R_5$ are hydrogen, X is methyl, Y is hydrogen, and the stereochemistry at $C_\beta$ is R;

i) n is 3, dashed line a is not present, the compound of formula II is an acid, $R_4$ and $R_5$ are hydrogen, X is methyl, Y is hydrogen, and the stereochemistry at $C_\beta$ is S;

j) n is 3, dashed line a is not present, the compound of formula II is an acid, $R_4$ and $R_5$ are hydrogen, X is ethyl, Y is hydrogen, and the stereochemistry at $C_\beta$ is R;

k) n is 3, dashed line a is not present, the compound of formula II is an acid, $R_4$ and $R_5$ are hydrogen, X is ethyl, Y is hydrogen, and the stereochemistry at $C_\beta$ is S;

l) n is 2, dashed line a is not present, the compound of formula II is an acid, $R_4$ and $R_5$ are hydrogen, X is hydrogen, Y is methyl, and the stereochemistry at $C_\beta$ is R;

m) n is 2, dashed line a is not present, the compound of formula II is an acid, $R_4$ and $R_5$ are hydrogen, X is hydrogen, Y is ethyl, and the stereochemistry at $C_\beta$ is S;

n) n is 2, dashed line a is not present, the compound of formula II is an acid, $R_4$ is methyl, $R_5$ is hydrogen, X is hydrogen, Y is propyl, and the stereochemistry at $C_\beta$ is S;

o) n is 4, dashed line a is present, the compound of formula II is an acid, z is 2, $R_4$ and $R_5$ are hydrogen, and the stereochemistry at $C_\beta$ is R;

p) n is 3, dashed line a is present, the compound of formula II is an acid, z is 2, $R_4$ and $R_5$ are methyl, and the stereochemistry at $C_\beta$ is S;

q) n is 2, dashed line a is present, the compound of formula II is an acid, z is 3, $R_4$ is methyl, $R_5$ is hydrogen, and the stereochemistry at $C_\beta$ is R;

r) n is 3, dashed line a is not present, the compound of formula II is an acid, $R_5$ is hydrogen, $R_4$ is methyl, X is hydrogen, Y is ethyl, and the stereochemistry at $C_\beta$ is S;

s) n is 3, dashed line a is not present, the compound of formula II is an acid, $R_5$ is hydrogen, X is hydrogen, Y and $R_4$ are ethyl, and the stereochemistry at $C_\beta$ is S;

or the ester or salt thereof.

Preferably, the compound is one of the species a–k above.

In yet another embodiment, the present invention relates to a non-natural amino acid compound of the formula III:

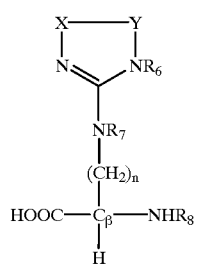

(III)

wherein n is an integer of from 2 to 4;

X–Y is $(CH_2)_z$, wherein z is an integer of from 2 to 4;

$R_6$, $R_7$ and $R_8$ are, independently, hydrogen or lower branched or straight chain alkyl, alkenyl or alkynyl of $C_1$–$C_5$; and $C_\beta$ is a carbon atom and the stereochemistry at $C_\beta$ is either R or S;

or the ester or salt thereof.

In one embodiment, $R_6$, $R_7$ and $R_8$ are independently, hydrogen or lower alkyl or straight chain alkyl of $C_1$–$C_5$, preferably hydrogen or methyl, even more preferably all are hydrogen. In another embodiment, z is 2 or 3, preferably 3. In a preferred embodiment, n is 3. In one embodiment, the compound is:

a) n is 3, z is 2, $R_6$, $R_7$ and $R_8$ are hydrogen, the compound of formula III is an acid, and the stereochemistry at $C_\beta$ is R;

b) n is 3, z is 2, $R_6$, $R_7$ and $R_8$ are hydrogen, the compound of formula III is an acid, and the stereochemistry at $C_\beta$ is S;

c) n is 3, z is 3, $R_6$, $R_7$ and $R_8$ are hydrogen, the compound of formula III is an acid, and the stereochemistry at $C_\beta$ is R;

d) n is 3, z is 3, $R_6$, $R_7$ and $R_8$ are hydrogen, the compound of formula III is an acid, and the stereochemistry at $C_\beta$ is S;

e) n is 2, z is 2, $R_6$, $R_7$ and $R_8$ are hydrogen, the compound of formula III is an acid, and the stereochemistry at $C_\beta$ is R;

f) n is 4, z is 2, $R_6$, $R_7$ and $R_8$ are hydrogen, the compound of formula III is an acid, and the stereochemistry at $C_\beta$ is S;

g) n is 2, z is 3, $R_6$, $R_7$ and $R_8$ are hydrogen, the compound of formula III is an acid, and the stereochemistry at $C_\beta$ is R;

h) n is 4, z is 3, $R_6$, $R_7$ and $R_8$ are hydrogen, the compound of formula III is an acid, and the stereochemistry at $C_\beta$ is S;

i) n is 2, z is 2, $R_6$, $R_7$ and $R_8$ are methyl, the compound of formula III is an acid, and the stereochemistry at $C_\beta$ is R;

j) n is 4, z is 2, $R_6$, $R_7$ and $R_8$ are methyl, the compound of formula III is an acid, and the stereochemistry at $C_\beta$ is S;

k) n is 2, z is 3, $R_6$, $R_7$ and $R_8$ are methyl, the compound of formula I is an acid, and the stereochemistry at $C_\beta$ is R;

l) n is 4, z is 3, $R_6$, $R_7$ and $R_8$ are methyl, the compound of formula III is an acid, and the stereochemistry at $C_\beta$ is S;

or the ester or salt thereof.

Preferably, the compound is one of the species a–d above.

The invention further relates to a non-natural amino acid compound of the formula IV:

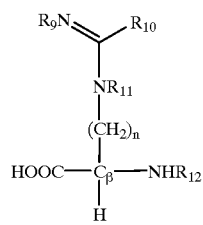

(IV)

wherein n is an integer of from 2 to 4;

$R_9$, $R_{10}$, $R_{11}$, and $R_{12}$ are, independently, hydrogen or lower branched or straight chain alkyl, alkenyl or alkynyl of $C_1$–$C_5$; and $C_\beta$ is a carbon atom and the stereochemistry at $C_\beta$ is either R or S;

or the ester or salt thereof.

In one embodiment, $R_9$, $R_{10}$, $R_{11}$, and $R_{12}$ are, independently, hydrogen or lower straight or branched chain alkyl of $C_1$–$C_5$, preferably hydrogen, methyl or ethyl. In another embodiment, $R_{10}$ is methyl. In a preferred embodiment, $R_9$ is hydrogen, $R_{10}$ is methyl, $R_{12}$ is hydrogen, and n is 3. In one embodiment, the compound is:

a) n is 3, $R_9$, $R_{11}$, and $R_{12}$ are hydrogen, $R_{10}$ is methyl, the compound of formula IV is an acid, and the stereochemistry at $C_\beta$ is R;

b) n is 3, $R_9$, $R_{11}$ and $R_{12}$ are hydrogen, $R_{10}$ is methyl, the compound of formula IV is an acid, and the stereochemistry at $C_\beta$ is S;

c) n is 3, $R_9$ and $R_{12}$ are hydrogen, $R_{10}$ and $R_{11}$ are methyl, the compound of formula IV is an acid, and the stereochemistry at $C_\beta$ is R;

d) n is 3, $R_9$ and $R_{12}$ are hydrogen, $R_{10}$ and $R_{11}$ are methyl, the compound of formula IV is an acid, and the stereochemistry at $C_\beta$ is S;

e) n is 3, $R_9$ and $R_{12}$ are hydrogen, $R_{10}$ is methyl, $R_{11}$, is ethyl, the compound of formula IV is an acid, and the stereochemistry at $C_\beta$ is R;

f) n is 3, $R_9$ and $R_{12}$ are hydrogen, $R_{10}$ is methyl, $R_{11}$ is ethyl, the compound of formula IV is an acid, and the stereochemistry at $C_\beta$ is S;

g) n is 2, $R_9$, $R_{11}$ and $R_{12}$ are hydrogen, $R_{10}$ is methyl, the compound of formula IV is an acid, and the stereochemistry at $C_\beta$ is R;

h) n is 2, $R_9$, $R_{11}$ and $R_{12}$ are hydrogen, $R_{10}$ is methyl, the compound of formula IV is an acid, and the stereochemistry at $C_\beta$ is S;

i) n is 2, $R_9$ and $R_{12}$ are hydrogen, $R_{10}$ and $R_{11}$ are methyl, the compound of formula IV is an acid, and the stereochemistry at $C_\beta$ is R;

j) n is 4, $R_9$ and $R_{12}$ are hydrogen, $R_{10}$ and $R_{11}$ are methyl, the compound of formula IV is an acid, and the stereochemistry at $C_\beta$ is S;

k) n is 4, $R_9$ and $R_{12}$ are hydrogen, $R_{10}$ is methyl, $R_{11}$ is ethyl, the compound of formula IV is an acid, and the stereochemistry at $C_\beta$ is R;

l) n is 4, $R_9$ and $R_{12}$ are hydrogen, $R_{10}$ is methyl, $R_{11}$ is ethyl, the compound of formula IV is an acid, and the stereochemistry at $C_\beta$ is S;

or the ester or salt thereof.

Preferably, the compound is one of the species a–f above.

The invention further relates to a non-natural amino acid compound of the formula XL:

$$\begin{array}{c} \text{(XL)} \\ \text{H} \quad R_{15} \\ | \quad |c \\ R_1 - C_\alpha - NR_2R_{13} \\ | \\ (CH_2)n \\ | \\ HOOC - C_\beta - NHR_3 \\ | \\ H \end{array}$$

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

or the ester or salt thereof, wherein when dashed line c is present, then $R_{15}$ is present, and when dashed line c is not present, then $R_{15}$ is not present; wherein when dashed line c is present, the compound is a salt comprising a counterion;

when dashed line c is not present, and $R_1$, $R_2$, $R_3$ and $R_{13}$ are all hydrogen, then n is not 2 or 3;

when dashed line c is not present, n is 2 or 3, $R_1$ and $R_{13}$ are hydrogen, and $R_2$ and $R_3$ are independently hydrogen or methyl with at least one of $R_2$ and $R_3$ being methyl, then the stereochemistry at $C_\beta$ is not S, and when dashed line c is not present, n is 4, and $R_1$, $R_2$, $R_3$ and $R_{13}$ are all hydrogen, then the stereochemistry at $C_\beta$ is not R.

In one embodiment, the compound of formula XL is:

(a) dashed line c is not present, n is 1, $R_1$, $R_2$, $R_3$, and $R_{13}$ are hydrogen, and the stereochemistry at $C_\beta$ is S;

(b) dashed line c is not present, n is 4, $R_1$, $R_2$, and $R_3$ are hydrogen, $R_{13}$ is methyl, and the stereochemistry at $C_\beta$ is S;

(c) dashed line c is not present, n is 1, $R_1$, $R_2$, and $R_3$ are hydrogen, $R_{13}$ is methyl, and the stereochemistry at $C_\beta$ is S;

(d) dashed line c is not present, n is 2, $R_1$, $R_2$, and $R_3$ are hydrogen, $R_{13}$ is methyl, and the stereochemistry at $C_\beta$ is S;

(e) dashed line c is not present, n is 3, $R_1$, $R_2$, and $R_3$ are hydrogen, $R_{13}$ is methyl, and the stereochemistry at $C_\beta$ is S;

(f) dashed line c is not present, n is 1, $R_1$ and $R_3$ are hydrogen, $R_2$ and $R_{13}$ are methyl, and the stereochemistry at $C_\beta$ is S;

(g) dashed line c is not present, n is 2, $R_1$ and $R_3$ are hydrogen, $R_2$ and $R_{13}$ are methyl, and the stereochemistry at $C_\beta$ is S;

(h) dashed line c is not present, n is 3, $R_1$ and $R_3$ are hydrogen, $R_2$ and $R_{13}$ are methyl, and the stereochemistry at $C_\beta$ is S;

(i) dashed line c is present, n is 1, $R_1$ and $R_3$ are hydrogen, $R_2$, $R_{13}$, and $R_{15}$ are methyl, the counterion is bromide, and the stereochemistry at $C_\beta$ is S;

(j) dashed line c is present, n is 2, $R_1$ and $R_3$ are hydrogen, $R_2$, $R_{13}$, and $R_{15}$ are methyl, the counterion is bromide, and the stereochemistry at $C_\beta$ is S; and (k) dashed line c is present, n is 3, $R_1$ and $R_3$ are hydrogen, $R_2$, $R_{13}$, and $R_{15}$ are methyl, the counterion is bromide, and the stereochemistry at $C_\beta$ is S.

The invention further relates to a non-natural amino acid compound having the formula LX:

$$\begin{array}{c} \text{(LX)} \\ \text{H} \quad R_{15} \\ | \quad |c \\ R_1 - C_\alpha - NR_2R_{13} \\ | \\ (CH_2)n \\ | \\ HOOC - C_\beta - N_3 \\ | \\ H \end{array}$$

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

or the ester or salt thereof, wherein when dashed line c is present, then $R_{15}$ is present, and when dashed line c is not present, then $R_{15}$ is not present; wherein when dashed line c is present, the compound is a salt comprising a counterion.

In one embodiment, the stereochemistry at $C_\beta$ of LX is S. In another embodiment, $R_1$, $R_2$, and $R_{13}$ are, independently, hydrogen or methyl, and $R_{15}$ is methyl. In another embodiment, the compound has the formula LX, dashed line c is not present, n is 3, $R_1$, $R_2$, and $R_{13}$ are hydrogen, and the stereochemistry at $C_\beta$ is S. In another embodiment, the compound has the formula LX, dashed line c is not present, n is 3, $R_1$, $R_2$, and $R_{13}$ are methyl, and the stereochemistry at $C_\beta$ is S. In another embodiment, the compound has the formula LX, dashed line c is present, n is 3, $R_1$, $R_2$, and $R_{13}$ are hydrogen, $R_{15}$ is methyl, and the stereochemistry at $C_\beta$ is S. In another embodiment, the compound has the formula LX, dashed line c is present, n is 3, $R_1$, $R_2$, $R_{13}$ and $R_{15}$ are methyl, and the stereochemistry at $C_\beta$ is S.

The invention also relates to a non-natural amino acid compound of the formula LXX:

$$\begin{array}{c} \text{(LXX)} \\ HN - Y \\ \diagup \quad \diagdown_a \\ R_4N = \quad \quad X \\ \diagdown \diagup \\ N \\ | \\ (CH_2)n \\ | \\ HOOC - C_\beta - N_3 \\ | \\ H \end{array}$$

wherein n is an integer of from 2 to 4;

when dashed line a is not present, X and Y are independently, hydrogen or lower branched or straight chain alkyl, alkenyl or alkynyl of $C_1$–$C_5$;

when dashed line a is present, X–Y is $(CH_2)_z$, wherein z is an integer of from 2 to 4;

$R_4$ is hydrogen or lower branched or straight chain alkyl, alkenyl or alkynyl of $C_1$–$C_5$; and $C_\beta$ is a carbon atom and the stereochemistry at $C_\beta$ is either R or S;

or the ester or salt thereof.

The invention further relates to a nonnatural amino acid compound of the formula LXXX:

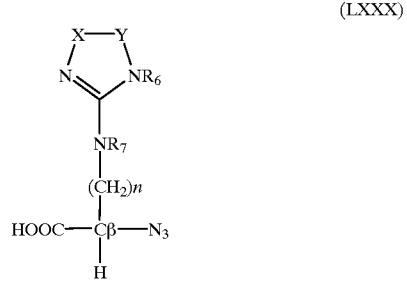

(LXXX)

wherein n is an integer of from 2 to 4;

X–Y is $(CH_2)_z$, wherein z is an integer of from 2 to 4;

$R_6$ and $R_7$ are, independently, hydrogen or lower branched or straight chain alkyl, alkenyl or alkynyl of $C_1$–$C_5$; and $C_\beta$ is a carbon atom and the stereo chemistry at $C_\beta$ is either R or S;

or the ester or salt thereof.

The invention also relates to a non-natural amino acid compound of the formula XC:

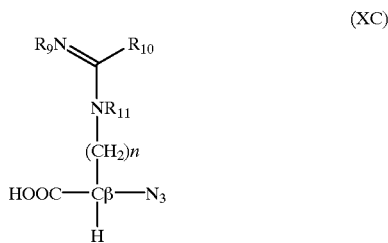

(XC)

wherein n is an integer of from 2 to 4;

$R_9$, $R_{10}$, and $R_{11}$ are, independently, hydrogen or lower branched or straight chain aLkyl, alkenyl or alkynyl of $C_1$–$C_5$; and $C_\beta$ is a carbon atom and the stereochemistry at $C_\beta$ is either R or S; or the ester or salt thereof.

In one embodiment, the structures of the non-natural amino acids of formula I, XL, and LX and the non-natural amino acids of formula II–IV, LXX, LXXX, and XC are similar to and closely replicate those of the naturally occurring amino acids lysine and arginine, respectively. In preferred embodiments, the compounds of the invention differ from the natural amino acids lysine and arginine, due, inter alia, a longer or shorter methylene bridge between the (i) amino/carboxyl terminus, which forms the bond between other amino acids in a peptide and (ii) the opposite functional terminus of the amino acid, preferably, the extended bridge of the invention compared to the natural amino acid bridge is one carbon length longer or shorter (i.e., the homo- or des-forms). In other preferred embodiments, the compounds of the invention have, inter alia, longer, shorter, or equivalent methylene bridge lengths and have substitutions at various moieties, form different moieties, or link moieties to form ring structures, compared to the comparable natural amino acid.

The design basis for all of the non-natural amino acids is the ability of positively-charged side chains to form electrostatic interactions (ion pairs or salt bridges) with negatively charged amino acids that can be influenced by the local environment (i.e. the structure of the amino acid.) In particular, placing an alkyl group in the vicinity of the charge destabilizes solvation of the ion and favors formation of an ion pair. Thus, the charged non-natural amino acids, when substituted in biologically active molecules for positively charged natural amino acids, can make the molecule bind better to its target if the natural amino acid is involved in binding. Since biological activity typically correlates directly with binding strength, more biologically active molecules can be created.

Each of the compounds can be prepared as the acid, salt or ester. In water, the non-natural amino acids of the present invention will be charged; however, in cell membranes and other non-polar regions of the cell, the non-natural amino acids may not be charged. In one embodiment, the ester group of the non-natural amino acids of the present invention is methyl, ethyl, t-BOC or FMOC. In another embodiment, the counter-ion for the salts of the non-natural amino acids is sodium, potassium, ammonium, chloride or bromide.

Particular non-natural amino acid compounds of the invention represented by formula I can be produced according to Scheme A:

Scheme A

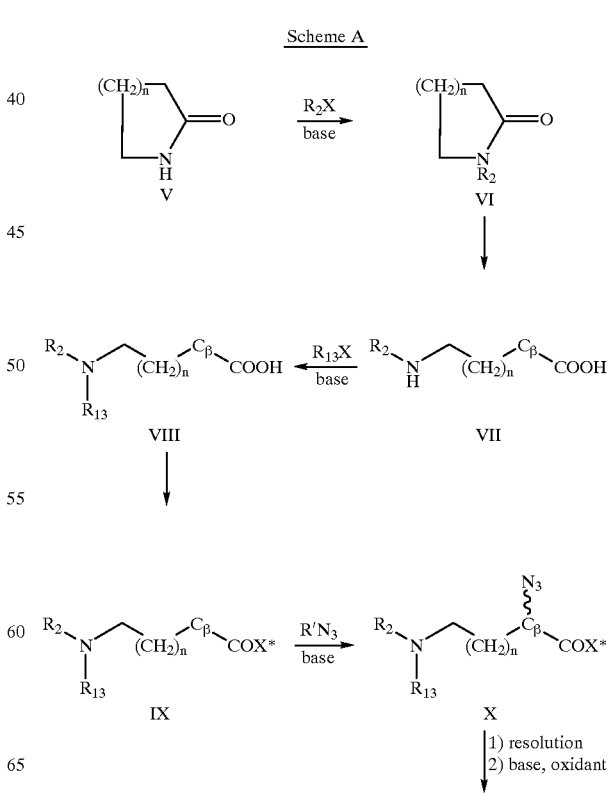

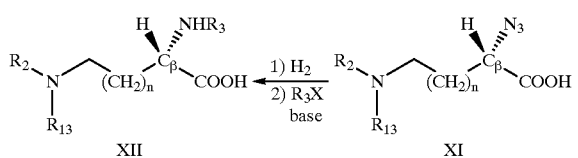

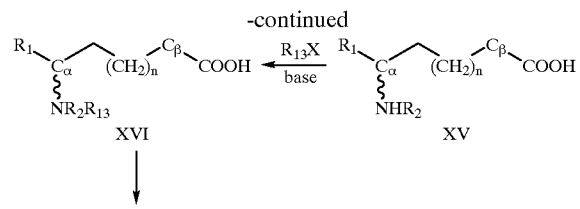

The cyclic lactam compound V (n is 2 to 4) is commercially available from Aldrich Chemical Company. Alkylation of the amide group of the cyclic lactam V with an alkylating agent $R_2X$ and a base generates the N-alkyl compound VI. In one embodiment, n is from 2 to 4. In a preferred embodiment, the alkylating agent $R_2X$ is methyl iodide and the base is sodium hydride. Treatment of V or VI with NaOH, generates the ring-open compound VII. Protection of the amino group can be accomplished by the addition of a base and a protecting group to a solution of VII in water. In a preferred embodiment, the base is sodium carbonate and the protecting group is di-tert-butyl dicarbonate. In another embodiment, treatment of VII with a base, preferably NaOH, NaH or LDA, and an alkylating agent $R_3$, X, preferably X is iodide m generates compound VIII. Compound VIII can be initially converted to an anhydride, preferably to the tert-butyl anhydride, followed by the addition of the conjugate base of a chiral auxiliary to generate IX. In a preferred embodiment, the chiral auxiliary is S-4-benzyl-2-oxazolidinone; however, the other enantiomer of the chiral auxiliary can be used as well. The addition of a base, preferably potassium hexamethyldisilazide, to IX generates an enolate, which can be quenched with an azide agent, preferably trisyl azide. Separation of the diastereoisomers of X can be accomplished by HPLC using hexane/ethyl acetate, preferably in a 1:1 ratio, as eluent. Cleavage of the chiral auxiliary to generate the acid compound XI requires a basic, oxidizing reaction media. In one embodiment, LiOH and hydrogen peroxide can be used. In one embodiment, this is a procedure for producing a non-natural amino acid having the formula LX. Hydrogenolysis of the azide compound XI in the presence of a catalyst, preferably Pd-C, converts the azide group to the primary amine. The amino group can be then deprotonated with a base, preferably triethylamine, and can be treated with an alkylating agent $R_3X$, preferably X is iodide, to generate compound XII, which is a non-natural amino acid compound represented by formula I.

Particular non-natural amino acid compounds of the invention represented by formula I can be produced according to Scheme B:

Scheme B

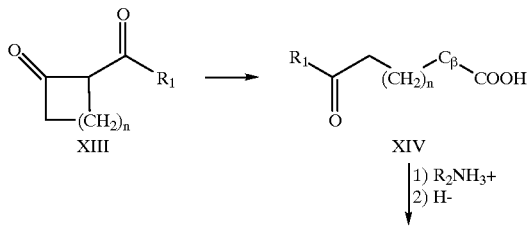

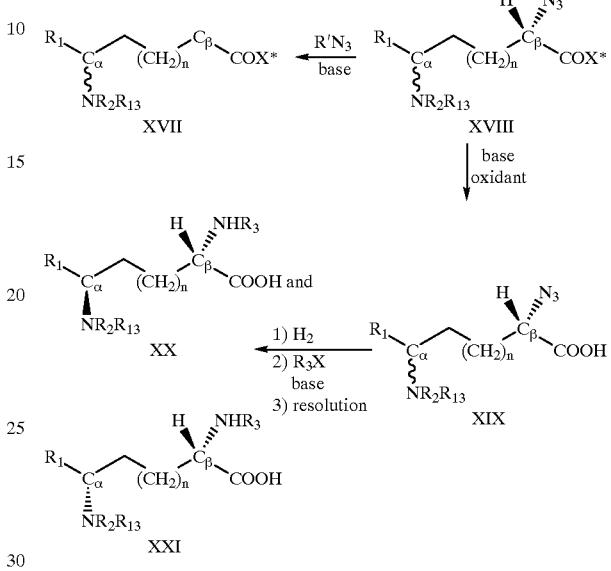

The addition of hydroxide, preferably NaOH, to a solution to XIII can produce the ring-open complex XIV. In the case of XIII, when n is 2 or 3, then these compounds are commercially available (Aldrich Chemical Company). When n is 1, then compound XIII can be prepared by deprotonating cyclobutanone with a base to generate the enolate followed by quenching with an acyl halide [$R_1(O)X$], where X is chloride, bromide or iodide. The addition of an amine salt to XIV initially generates an imineacid complex. In one embodiment, the amine salt is methylamine hydrochloride. In another embodiment, the addition of liquid $NH_3$ can produce the imineacid. Reduction of the imineacid with a reducing agent, preferably sodium cyanoborohydride, can generate the amino complex XV. Protection of the amino group can be accomplished by the addition of a base and a protecting group to XV. In one embodiment, the base is sodium carbonate and the protecting group is di-tert-butyl dicarbonate. In another embodiment, XV can be treated with a base, preferably NaOH, NaH or LDA, and an alkylating agent $R_{13}X$, preferably X is iodide, to generate compound XVI. Compound XVI can be initially converted to an ester, preferably to the tert-butyl ester, followed by the addition of the conjugate base of a chiral auxiliary to generate XVII. In a preferred embodiment, the chiral auxiliary is S-4-benzyl-2-oxazolidinone; however, the other enantiomer of the chiral auxiliary can be used as well. The addition of a base, preferably potassium hexamethyldisilazide, to XVII generates an enolate, which can be quenched with an azide agent, preferably trisyl azide (Compound XVIII). Cleavage of the chiral auxiliary to generate the acid compound XIX requires a basic, oxidizing reaction media. In one embodiment, LiOH and hydrogen peroxide can be used. In one embodiment, this is a procedure for producing a non-natural amino acid having the formula LX. Hydrogenolysis of XIX in the presence of a catalyst, preferably Pd—C, converts the azide group to the primary amine. The amino group can be deprotonated with a base, preferably sodium bicarbonate, and treated with a protecting agent. In one embodiment, the protecting agent is N-(9H-fluoren-2-ylmethoxycarbonyloxy)succinimide. In another embodiment, an alkylating agent $R_3X$, preferably X is iodide, can be added to generate a racemic mixture comprising of compounds XX and XXI. The diasteroisomers can be separated by HPLC with hexane/ethyl acetate as the eluent. When an amino group is protected with a N-(9H-fluoren-2-ylmethoxycarbonyloxy) group ($R_3$=FMOC), it is readily cleaved off when treated with an amine, preferably piperidine. Compounds XX and XXI are non-natural amino acid compounds represented by the formula I.

In another embodiment, non-natural amino acids having the formula XL can be prepared by adding an amine (e.g., $NHR_2R_{13}$ or $NR_2R_{13}R_{15}$) to a precursor having a leaving group. In one embodiment, the leaving group is an organic group. Examples of organic leaving groups include, but are not limited to, an alkoxide, a carboxylate, a carbonate, or a siloxy group. In another embodiment, the leaving group is a halide g group, more preferably a chloro or bromo group. For example, the addition of dimethylamine to compound A results in the formation of the neutral, non-natural amino acid B (eq. 1). In another embodiment, a trialkylamine (e.g., trimethylamine) can be added to compound A to produce the non-natural amino acid C as a salt (eq. 2). In this embodiment, compound C is represented by formula XL, where dashed line c is present, and the counterion is bromide.

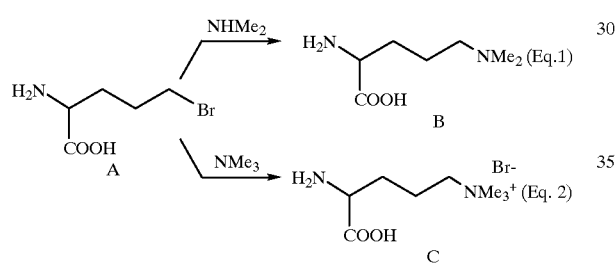

Particular non-natural amino acid compounds of the invention represented by formula II can be produced according to Scheme C:

Scheme C

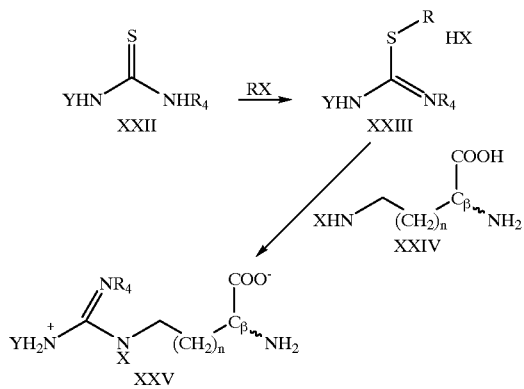

An alkylating agent was added to a solution of thiourea XXII. The acyclic thiourea complex XXII is commercially available. In one embodiment, the alkylating agent is methyl iodide, the thiourea is N-ethyl thiourea, and the solvent is acetone. After refluxing, an organic solvent, preferably hexane, was added, and the solution was cooled to 0° C. White crystals of XXIII were isolated and dried under reduced pressure. Compounds XXIII and XXIV were dissolved in NaOH and stirred at room temperature. In one embodiment, the concentration of NaOH is 2 N, and the solution was stirred for nine days at room temperature. The solution was brought to neutral pH by the addition of an acid, preferably concentrated HCl. The solution can be chromatographed with an eluent, preferably ammonium hydroxide, and even more preferably 1 M ammonium hydroxide. In one embodiment, the column can be a strongly-acidic cation exchange resin. Removal of solvent affords compound XXV, a non-natural amino acid compound having the formula II as the ammonium salts.

Particular non-natural amino acid compounds of the invention represented by formula III can be produced according to Scheme D:

Scheme D

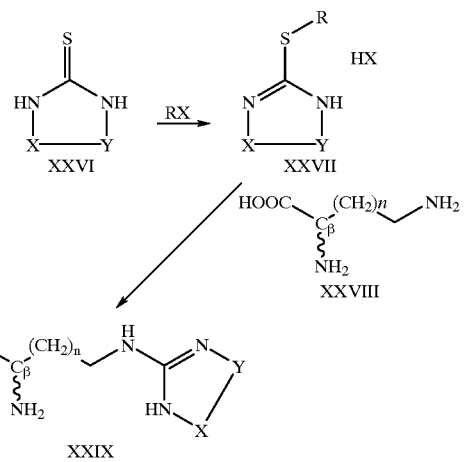

An alkylating agent was added to a solution of the cyclic thiourea XXVI. The cyclic thiourea complex XXVI is commercially available. In one embodiment, the alkylating agent is methyl iodide. In a preferred embodiment, the cyclic thiourea is a five- or six-member ring, and the solvent is acetone. After refluxing, an organic solvent, preferably hexane, was added, and the solution was cooled to 0° C. White crystals of XXVII were isolated and dried under reduced pressure. Compounds XXVII and XXVIII were dissolved in NaOH and stirred at room temperature. In one embodiment, the concentration of NaOH is 1 N. In another embodiment, the solution was refluxed for 4 hours then cooled to room temperature. The solution pH can be lowered by the addition of an acid. In one embodiment, the acid is HCl and the pH is 4. The solution can be chromatographed with an eluent, preferably ammonium hydroxide, and even more preferably 1.5 N ammonium hydroxide. In one embodiment, the column is a strongly-acidic cation exchange resin. Removal of solvent affords compound XXIX, a non-natural amino acid compound having the formula III.

Particular non-natural amino acid compounds of the invention represented by formula IV can be produced according to Scheme E:

Scheme E

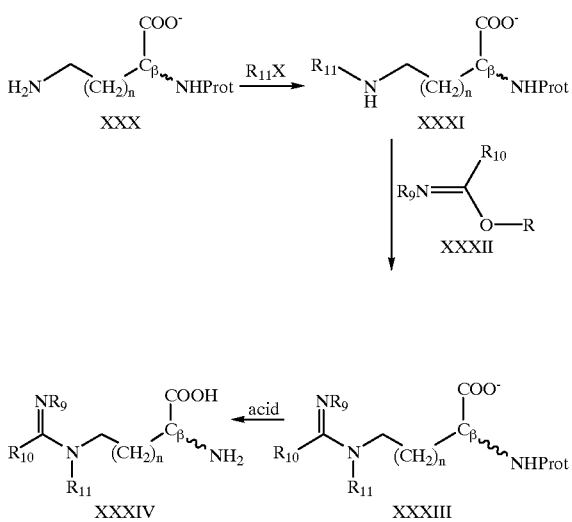

Protection of the i-amino group of an amino acid generates compound XXX. In one embodiment, the protecting group is BOC. The addition of an alkylating agent $R_{11}X$ in the presence of a base produces the N-alkyl compound XXXI. In a preferred embodiment, the alkylating agent is methyl iodide and the base is sodium bicarbonate. The acetimidate XXXII is added to a solution of XXXI. In one embodiment, methyl acetimidate is preferred. In another embodiment, the solvent is MeOH, and the solution was stirred at an elevated temperature, preferably 70° C., for 4 hours. Solvent was removed under reduced pressure and the residue can be subjected to chromatography. In one embodiment, silica gel chromatography is preferred in order to isolate compound XXXIII. Deprotection of the α-amino group of XXXIII can be accomplished by the addition of an acid. In a preferred embodiment, the protecting group is BOC and the acid is trifluoroacetic acid. Removal of the protecting group generates compound XXXIV, a non-natural amino acid compound having the formula IV.

In another embodiment, the compounds having the formula LXX, LXXX, and XC can be prepared by using the starting material L shown below.

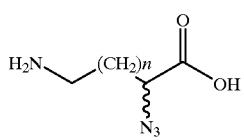

(L)

For example, compound L can be substituted for compound XXIV in Scheme C to produce the compounds having the formula LXX. Similarly, compound XXVIII in Scheme D and compound XXX in Scheme E can be substituted with L to produce compounds having the formulas LXXX and XC, respectively. Compound L can be prepared using techniques known in the art. In one embodiment, compound L can be prepared by the procedure depicted in Scheme K.

Scheme K

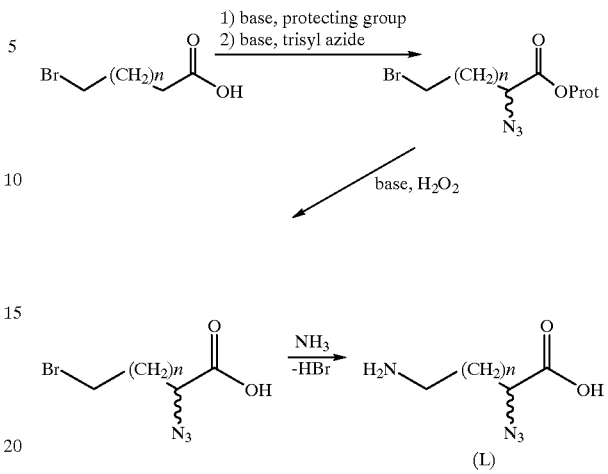

In another embodiment, the invention relates to a peptide containing a compound having the formula I, II, III, IV, XL, LX, LXX, LXXX, and/or XC. All peptides were synthesized by the Merrifield solid phase method, which is an established method for preparing peptides to those skilled in the art. All compounds having the formulas I–IV, and XL can be protected at the α-amino group with standard protecting groups. In a preferred embodiment, the protecting groups are BOC and FMOC. The non-natural amino acids having the formulas I–IV, XL, LX, LXX, LXXX, and/or XC can be substituted in any desired peptide, wherein the substitution is site-specific.

Screening of Non-Natural Amino Acid-containing Peptides

The invention provides a method for screening a peptide for an activity or pharmacological activity, comprising the steps of: a) measuring an activity or pharmacological activity of a peptide having a selected amino acid sequence and comprising a natural amino acid; b) measuring the same activity or pharmacological activity of a peptide having the same amino acid sequence but substituted independently in place of at least one natural amino acid, is a non-natural amino acid having the formula I–IV, XL, LX, LXX, LXXX, and/or XC described above; and c) comparing the measured activity or pharmacological activity of the peptides from steps a) and b) to determine whether the peptide of step b) has the activity or pharmacological activity.

The activities for which the present invention screens can include any activity associated with a biologically active peptide or peptidomimetic. The following is a partial list of the many activities that can be determined in the present screening method:

1. Receptor Agonist/Antagonist Activity

A compendia of examples of specific screens for measuring these activities can be found in: "The RBI Handbook of Receptor Classification and Signal Transduction" K. J. Watling, J. W. Kebebian, J. L. Neumeyer, eds. Research Biochemicals International, Natick, Mass., 1995, and references therein. Methods of analysis can be found in: T. Kenakin "Pharmacologic Analysis of Drug-Receptor Interactions" 2nd Ed. Raven Press, New York, 1993, and references therein.

2. Enzyme Inhibition

A compendia of examples of specific screens for measuring these activities can be found in: H. Zollner "Handbook of Enzyme Inhibitors", 2nd Ed. VCH Weinheim, FRG, 1989, and references therein.

3. Central Nervous System, Autonomic Nervous System (Cardiovascular and Gastrointestinal Tract), Antihistaminic, Anti-inflammatory, Anaesthetic, Cytotoxic, and Antifertility Activities A compendia of examples of specific screens for measuring these activities can be found in: E. B. Thompson, "Drug Bioscreening: Drug Evaluation Techniques in Pharmacology", VCH Publishers, New York, 1990, and references therein.

4. Anticancer Activities

A compendia of examples of specific screens for measuring these activities can be found in: I. J. Fidler and R. J. White "Design of Models for Testing Cancer Therapeutic Agents", Van Nostrand Reinhold Company, New York, 1982, and references therein.

5. Antibiotic and Antiviral (Especially anti-HIV) Activities

A compendia of examples of specific screens for measuring these activities can be found in: "Antibiotics in Laboratory Medicine", 3rd Ed., V. Lorian, ed. Williams and Wilkens, Baltimore, 1991, and references therein. A compendia of anti- HIV screens for measuring these activities can be found in: "HIV Volume 2: Biochemistry, Molecular Biology and Drug Discovery", J. Karn, ed., IRL Press, Oxford, 1995, and references therein.

6. Immunomodulatory Activity

A compendia of examples of specific screens for measuring these activities can be found in: V. St. Georgiev (1990) "Immunomodulatory Activity of Small Peptides" Trends Pharm. Sci. 11, 373–378.

7. Pharmacokinetic Properties

The pharmacological activities assayed in the screening method include half-life, solubility, or stability, among others. For example, methods of analysis and measurement of pharmacokinetic properties can be found in: J.-P. Labaune "handbook of Pharmacokinetics: Toxicity Assessment of Chemicals", Ellis Horwood Ltd., Chichester, 1989, and references therein.

In the screening method, the peptide of step a) can consist of natural amino acids. Alternatively, the peptide of step a) can contain mostly natural amino acids, but comprise one or a small number of non-natural amino acids. Such a peptide is considered to consist essentially of natural amino acids. Further in the alternative, the peptide of step a) can be mostly non-natural amino acids, but comprise one or a small number of natural amino acids. Such a peptide is considered to consist essentially of non-natural amino acids. In another alternative, the peptide of step a) can contain more than a small number and up to half non-natural amino acids or even up to mostly non-natural amino acids with the balance being natural amino acids.

In the screening method, the non-natural amino acid in the peptide of step b) can be substituted for the comparable at least one natural amino acid. The term "comparable" is used herein to denote a structurally similar molecule as described in detail above. In one embodiment, the structures of the non-natural amino acids of formula I, XL, and LX and the non-natural amino acids of formula II–IV, LXX, LXXX, and XC are similar to and closely replicate those of the naturally occurring amino acid, lysine and arginine, respectively.

Additionally, a screening method is provided in which the peptide of step b) can contain a non-natural amino acid of the present invention added to, rather than substituted for, a natural or non-natural amino acid in the peptide of step a).

Thus, in the screening method contemplated herein, any peptide having one or more of the present non-natural amino acids can be compared to any peptide having a known activity or pharmacological activity to determine whether or not it has the same or similar activity or pharmacological activity at the same or different level. Depending on the specifics of how the measuring step is carried out, the present screening method can also be used to detect an activity or pharmacological activity exhibited by the peptide of step b) that differs qualitatively from the activity or pharmacological activity of the peptide of step a). Also, the screening method can be used to detect and measure qualitative and quantitative differences in the same or similar activity or pharmacological activity.

Thus, the present invention takes account of the situation in which the structural differences of the non-natural amino acid significantly alter the activity of the peptide incorporating such a non-natural amino acid. Substitution of a natural amino acid with a non-natural amino acid in a peptide typically increases the hydrophobicity of the peptide, which can result indirectly in increased binding activity when the amino acid substituted is involved in binding (e.g., receptor-ligand binding, enzyme-cofactor binding, enzyme-substrate binding) and since binding strength is correlated with activity, a peptide higher potency (higher measured activity level) can result.

Furthermore, the non-natural amino acids of the present invention also enhance or increase the pharmacological activity of a peptide. For example, because the non-natural amino acids are more hydrophobic (i e., more lipophilic), a peptide containing a non-natural amino acid is more able to pass a body barrier (e.g., blood brain, blood ocular, skin, intestinal epithelium). Additionally, because the non-natural amino acids impart increased selectivity and stability to a peptide, the pharmacological activity can also be screened when compared to other peptides.

Treatment

The invention further relates to a method of treating or preventing in a subject a disease treated or prevented by the administration of a peptide comprising administering to the subject a peptide having, substituted for a natural amino acid, at least one non-natural amino acid having the formula I–IV, XL, LX, LXX, LXXX, and/or XC.

In one embodiment, the peptide used in the treatment method can be a peptide that usually contains a lysine or an arginine, but has at least one non-natural amino acid having the formula I–IV, XL, LX, LXX, LXXX, and/or XC substituted therefor. Alternatively, the peptide can contain neither of these amino acids, yet it can be effective to substitute a non-natural amino acid of the invention for another amino acid. In addition the peptide used in the treatment method can have one or more non-natural amino acid of the present invention added to the existing sequence of amino acids.

In the treatment method of the present invention, the diseases that can be treated and the peptides that can be used are numerous. A partial list of peptides and diseases is set out below.

Peptides for triggering B and T cell activity can be used to treat autoimmune disease, including uveitis, collagen-induced, adjuvant and rheumatoid arthritis, thyroiditis, myasthenia gravis, multiple sclerosis and diabetes. Examples of these peptides are interleukins (referenced in Aulitzky, W E; Schuler, M; Peschel, C.; Huber, C.; Interleukins. Clinical pharmacology and therapeutic use. Drugs. 48(5):667–77, November 1994) and cytokines (referenced in Peters, M.; Actions of cytokines on the immune response and viral interactions: an overview. Hepatology. 23(4):909–16, April 1996).

Enkephlin and analogs, agonists and antagonists can be used to treat AIDS, $ARC_\alpha$ and cancer, pain modulation, Huntington's, Parkinson's diseases.

LHRH and analogs, agonists and antagonists can be used to treat prostatic tumors and reproductive physiopathology, including breast cancer, and infertility.

Peptides and peptidomimetics that target crucial enzymes, oncogenes or oncogene products, tumor-suppressor genes and their products, growth factors and their corresponding receptors can be used to treat cancer. Examples of these peptides are described in Unger, C. Current concepts of treatment in medical oncology: new anticancer drugs. Journal of Cancer Research & Clinical Oncology. 122(4): 189–98, 1996.

Neuropeptide Y and other pancreatic polypeptides, and analogs, agonists and antagonists can be used to treat stress, anxiety, depression and associated vasoconstrictive activities.

Gluco-incretins, including gastric inhibitory polypeptide, glucose-dependent insulinotropic polypeptide and glucagon-like polypeptide-1 and analogs, agonists and antagonists can be used to treat Type II diabetic hyperglycaemia.

Atrial natriuretic factor and analogs, agonists and antagonists can be used to treat congestive heart failure.

Integrin and analogs, agonists and antagonists can be used to treat osteoporosis, scar formation, bone synthesis, inhibition of vascular occlusion, and inhibition of tumor invasion and metastasis.

Glucagon, glucagon-like peptide 1 and analogs, agonists and antagonists can be used to treat diabetes cardiovascular emergencies.

Antithrombotic peptides and analogs, agonists and antagonists can be used to treat cardiovascular and cerebrovascular diseases. Examples of these peptides RGD, D-Phe-Pro-Arg and others named are described in Ojima I.; Chakravarty S.; Dong Q. Antithrombotic agents: from RGD to peptide mimetics. Bio organic & Medicinal Chemistry. 3(4):337–60, 1995.

Cytokines/interleukins and analogs, agonists and antagonists can be used to treat inflammatory disease, immune response dysfunction, hematopoiesis, mycosis fungoides, aplastic anemia, thrombocytopenia, and malignant melanoma. Examples of these peptides are Interleukins, referenced in Aulitzky et al. and Peters et al.

Endothelin and analogs, agonists and antagonists can be used to treat arterial hypertension, myocardial infarction, congestive heart failure, atherosclerosis, shock conditions, renal failure, asthma and vasospasm.

Natriuretic hormones and analogs, agonists and antagonists can be used to treat cardiovasicular disease and acute renal failure. Examples of these peptides are named and described in Espiner, E. A;. Richards, A. M.; Yandle, T. G.; Nicholls, M. G.; Natriuretic hormones. Endocrinology & Metabolism Clinics of North America. 24(3):481–509, 1995.

Peptides that activate or inhibit tyro sine kinase, or bind to TK-activating or inhibiting peptides and analogs, agonists and antagonists can be used to treat chronic myelogenous and acute lymphocytic leukemias, breast and ovarian cancers and other tyrosine kinase associated diseases. Examples of these peptides are described in Smithgall, TE.; SH2 and SH3 domains: potential targets for anti-cancer drug design. Journal of Pharmacological & Toxicological Methods. 34(3) :125–32, 1995.

Renin inhibitors analogs, agonists and antagonists can be used to treat cardiovascular disease, including hypertension and congestive heart failure. Examples of these peptides are described in Rosenberg, S. H.; Renin inhibition. Cardiovascular Drugs & Therapy. 9(5):645–55, 1995.

Angiotensin-converting enzyme inhibitors, analogs, agonists and antagonists can be used to treat cardiovascular disease, including hypertension and congestive heart failure.

Peptides that activate or inhibit tyrosine phosphorylases can be used to treat cardiovascular diseases. Examples of these peptides are described in Srivastava, A. K.; Protein tyrosine phosphorylation in cardiovascular system Molecular & Cellular Biochemistry. 149–150:87–94, 1995.

Peptide based antivirals can be used to treat viral diseases. Examples of these peptides are described in Toes, R. E.; Feltkamp, M. C.; Ressing, M. E.; Vierboom, M. P.; Blom, R. J.; Brandt, R. M ; Hartman, M.; Offinga, R.; Melief, C. J.; Kast, W. M.; Cellular immunity against DNA tumour viruses: possibilities for peptide-based vaccines and immune escape. Biochemical Society Transactions. 23(3):692–6, 1995.

Corticotropin releasing factor and peptide analogs, agonists and antagonists can be used to treat disease associated with high CRF, i.e Alzheimer's disease, anorexia nervosa, depressive, psycotic disorders, arthritis, and multiple sclerosis.

Peptide agonists and antagonists of platelet-derived wound-healing formula (PDWHF) can be used as a therapy for donor tissue limitations and wound-healing constraints in surgery. Examples of these peptides are described in Rudkin, G. H.; Miller, T. A.; Growth factors in surgery. Plastic & Reconstructive Surgery. 97(2):469–76, 1996.

Fibronectin, fibribnopeptide inhibitors and analogs, agonists and antagonists can be used to treat metastasis (i.e. enzyme inhibition, tumor cell migration, invasion, and metastasis).

Chemokines (types of cytokine, including interleukin-8, RANTES, and monocyte chemotactic peptide) analogs, agonists and antagonists can be used to treat arthritis, hypersensitivity, angiogenesis, renal disease, glomerulonephritis, inflammation, and hematopoiesis.

Neutral endopeptidase inhibitors and analogs, agonists and antagonists can be used to treat hypertension and inflammation. Examples of these peptides are described in Gregoire, J. R; Sheps, S. G; Newer antihypertensive drugs. Current Opinion in Cardiology. 10(5):445–9, 1995.

Substance P and analogs, agonists and antagonists can be used to treat immune system dysfunction, pain transmission/perception and in autonomic reflexes and behaviors.

Alpha-melanocyte-stimulating hormone and analogs, agonists and antagonists can be used to treat AIDS, rheumatoid arthritis, and myocardial infarction.

Bradykinin (BK) and analogs, agonists and antagonists can be used to treat inflammatory diseases (edema, etc), asthma, allergic reactions (rhinitis, etc), anesthetic uses, and septic shock.

Secretin can be used to treat cardiovascular emergencies.

GnRH and analogs, agonists and antagonists can be used to treat hormone-dependent breast and prostate tumors.

Somatostatin and analogs, agonists and antagonists can be used to treat gut neuroendocrine tumors.

Gastrin, Gastrin Releasing Peptide and analogs, agonists and antagonists can be used as an adjuvant to chemotherapy or surgery in small cell lung cancer and other malignancies, or to treat allergic respiratory diseases, asthma and allergic rhinitis.

Laminin-derived synthetic peptides analogs, agonists and antagonists can be used to treat tumor cell growth, angiogenesis, regeneration studies, vascularization of the eye with diabetes, and ischemia. Examples of these peptides are described in Kleinman, H. K.; Weeks, B. S.; Schnaper, H. W.; Kibbey, M. C.; Yamamura, K; Grant, D. S; The laminins: a family of basement membrane glycoproteins important in cell differentiation and tumor metastases. Vitamins & Hormones. 47:161–86, 1993.

Defensins, corticostatins, dermaseptins, mangainins, and other antibiotic (antibacterial and antimicrobial) peptides and analogs, agonists and antagonists can be used to treat infections, tissue inflammation and endocrine regulation.

Vasopressin and analogs, agonists and antagonists can be used to treat neurological disorders, stress and Diabetes insipidus.

Oxytocin and analogs, agonists and antagonists can be used to treat neurological disorders and to induce labor.

ACTH-related peptides and analogs, agonists and antagonists can be used as neurotrophic, neuroprotective, and peripheral demyelinating neuropathy agents.

Amyloid-beta peptide and analogs, agonists and antagonists can be used to treat Alzheimer's disease.

Epidermal growth factor, receptor, and analogs, agonists and antagonists can be used to treat necrotizing enterocolitis, Zollinger-Ellison syndrome, gastrointestinal ulceration, colitis, and congenital microvillus atrophycarcinomas.

Leukocyte adhesion molecules and their ligands, and analogs, agonists and antagonists can be used to treat atherosclerosis, inflammation. Examples of these peptides are described in Barker, J. N.; Adhesion molecules in cutaneous inflammation. Ciba Foundation Symposium 189:91–101.

Major histocompatibility complex (MHC) binding peptides and analogs, agonists and antagonists can be used to treat autoimmune, immunodysfunctional, immuno modulatory diseases and as well as used for their corresponding therapies. Examples of these peptides are described in Appella, E.; Padlan, E. A.; Hunt, D. F; Analysis of the structure of naturally processed peptides bound by class I and class II major histocompatibility complex molecules. EXS. 73:105–19, 1995.

Corticotropin releasing factor can be used to treat neurological disorders.

Neurotrophins (including brain-derived neurotrophic factor (BDNF), nerve growth factor, and neurotrophin 3) and analogs, agonists and antagonists can be used to treat neurological disorders.

Cytotoxic T-cell activating peptides can be used to treat infectious diseases and cancer. Examples of these peptides are described in: Chesnut R. W.; Sette, A.; Celis, E.; Wentworth, P.; Kubo, R. T.; Alexander, J.; Ishioka, G.; Vitiello, A.; Grey, H. M; Design and testing of peptide-based cytotoxic T-cell-mediated immunotherapeutics to treat infectious diseases and cancer. Pharmaceutical Biotechnology. 6:847–74, 1995.

Peptide immunogens for prevention of HIV-1 and HTLV-I retroviral infections can be used to treat AIDS. Examples of these peptides are described in Hart, M. K.; Palker, T. J.; Haynes, B F; Design of experimental synthetic peptide immunogens for prevention of HIV-1 and HTLV-I retroviral infections. Pharmaceutical Biotechnology. 6:821–45, 1995.

Galanin and analogs, agonists and antagonists can be used to treat Alzheimer's disease, depression, eating disorders, chronic pain, prevention of ischemic damage, and growth hormone modulation.

Tachykinins (neurokinin A and neurokinin B) and analogs, agonists and antagonists can be used to treat pain transmission/perception and in autonomic reflexes and behaviors.

RGD containing peptides can be used to treat various diseases involved with cell adhesion, antithrombotics, and acute renal failure.

Osteogenic growth peptide and analogs, agonists and antagonists can be used as treatment of systemic bone loss. Examples of these peptides are described in Bab IA. Regulatory role of osteogenic growth peptide in proliferation, osteogenesis, and hemopoiesis. Clinical Orthopaedics & Related Research (313):64–8, 1995.

Parathyroid hormone, parathyroid hormone related-peptide and analogs, agonists and antagonists can be used to treat diseases affecting calcium homeostasis (hypercalcemia), bone metabolism, vascular disease, and atherosclerosis.

Kallidin and analogs, agonists and antagonists can be used to treat tissue injury or inflammation and pain signaling pathological conditions of the CNS.

T cell receptor peptide vaccines and analogs, agonists and antagonists can be used in immunotherapy. Examples of these peptides are described in Brostoff, S W; T cell receptor peptide vaccines as immunotherapy. Agents & Actions—Supplements. 47:53–8, 1995.

Platelet-derived growth factor (PDGF) and analogs, agonists and antagonists can be used to treat non-neoplastic hyperproliferative disorders, therapy for donor tissue limitations and wound-healing constraints in surgery.

Amylin, calcitonin gene related peptides (CGRP) and analogs, agonists and antagonists can be used to treat insulin-dependent diabetes.

Vasoactive intestinal polypeptide and analogs, agonists and antagonists can be used to treat allergic respiratory diseases, asthma and allergic rhinitis, and nervous control of reproductive functions.

Growth hormone-releasing hormone and analogs, agonists and antagonists can be used to treat growth hormone deficiency and immunomodulation.

HIV protease inhibiting peptides can be used to treat AIDS. Examples of these peptides are described in Bugelski, P. J.; Kirsh, R.; Hart, T. K; HIV protease inhibitors; effects on viral maturation and physiologic function in macrophages. Journal of Leukocyte Biology. 56(3):374–80, 1994.

Thymopoietin active fragment peptides and analogs, agonists and antagonists can be used to treat rheumatoid arthritis and virus infections.

Cecropins and analogs, agonists and antagonists can be used as antibacterials.

Thyroid releasing hormone and analogs, agonists and antagonists can be used to treat spinal cord injury and shock.

Erythropoietin and analogs, agonists and antagonists can be used to treat anemia.

Fibroblast growth factor (FGF), receptor and analogs, agonists and antagonists can be as stimulation of bone formation, as well as used as a treatment for Kaposi's sarcoma, neuron regeneration, prostate growth, tumor growth inhibition, and angiogenesis.

Stem cell factor and analogs, agonists and antagonists can be used to treat anemias.

GP120, GP160, CD4 fragment peptides and analogs, agonists and antagonists can be used to treat AIDS.

Insulin-like growth factor, receptor, and analogs, agonists and antagonists can be used to treat breast and other cancers, noninsulin-dependen diabetest mellitus, cell proliferation, apoptosis, hematopoiesis, AIDS, growth disorders, osteoporosis,and insulin resistance.

Colony stimulating factors (granulocyte-macrophage colony-stimulating factor, granulocyte colony-stimulating factor, and macrophage colony-stimulating factor and analogs, agonists and antagonists can be used to treat anemias.

Kentsin and analogs, agonists and antagonists can be used for immunomodulation.

Lymphocyte activating peptide and analogs, agonists and antagonists can be used for immunomodulation. Examples of these peptides are described in Loleit, M.; Deres, K.; Wiesmuller, K. H.; Jung, G.; Eckert, M.; Bessler, W. G; Biological activity of the *Escherichia coli* lipoprotein: detection of novel lymphocyte activating peptide segments of the molecule and their conformational characterization. Biological Chemistry Hoppe-Seyler. 375(6):407–12, June 1994.

Tuftsin and analogs, agonists and antagonists can be used for immunomodulation.

Prolactin and analogs, agonists and antagonists can be used to treat rheumatic diseases, systemic lupus erythematosus, hyperprolactemia.

Angiotensin II and receptor(s) and analogs, agonists and antagonists can be used to treat hypertension, hemodynamic regulation, neurological disorders, diabetic nephropathies, aortoarterities induced RVH, hyperaldosteronism, heavy metal induced cardiovascular effects, diabetes mellitus and thyroid dysfunction.

Dynorphin and analogs, agonists and antagonists can be used to treat neurological disorders, pain management, algesia, spinal cord injury and epilepsy.

Calcitonin, and analogs, agonists and antagonists can be used to treat neurological disorders, immune system dysfunction, calcium homeostasis, and osteoporosis.

Pituitary adenylate cyclase activating polypeptide can play a role in growth, signal transduction vasoactivity roles, exact role in diseases not determined yet.

Cholecystokinin and analogs, agonists and antagonists can be used to treat feeding disorders, panic disorders, and anti-opioid properties.

Pepstatin and analogs, agonists and antagonists can be used a pepsin and HIV protease inhibitor (AIDS).

Bestatin and analogs, agonists and antagonists can be used to treat muscular dystrophy, anticancer, antileukemia, immune response modulator, and acute non-lymphocytic leukemia.

Leupeptin and analogs, agonists and antagonists can be used as a protease inhibitor, exact role in diseases not determined yet.

Luteinizing hormone and releasing hormone and analogs, agonists and antagonists can be used as a infertility male contraceptive.

Neurotensin and analogs, agonists and antagonists can be used as a antipsychotic and analgesic agent.

Motilin and analogs, agonists and antagonists can be used as for the control of gastric emptying.

Insulin and analogs, agonists and antagonists can be used to treat diabetes.

Transforming growth factor (TGF) and analogs, agonists and antagonists can be used for cell proliferation and differentiation, cancer treatment, immunoregulation, therapy for donor tissue limitations, and wound-healing constraints in surgery.

Bone morphogenetic proteins (BMPs) and analogs, agonists and antagonists can be used as therapy for donor tissue limitations, osteogenesis, and wound-healing constraints in surgery.

Bombesin and analogs, agonists and antagonists can be used to prevent the proliferation of tumor cells, modulation of feeding, and neuroendocrine functions.

Glucagon, glucagon-like peptide 1 and analogs, agonists and antagonists can be used to treat diabetes cardiovascular emergencies.

Pancreastatin, chromogranins A, B and C and analogs, agonists and antagonists—conditions associated with inhibition of insulin secretion, exocrine pancreatic secretion and gastric acid secretion, and stimulation of glucagon secretion.

Endorphins and analogs, agonists and antagonists can be used to treat neurological disorders, alleviating pain, treatment of opioid abuse, obesity, and diabetes. Examples of these peptides are named and described in Dalayeun, J. F.; Nores, J. M.; Bergal, S.; Physiology of beta-endorphins. A close-up view and a review of the literature. Biomedicine & Pharmacotherapy. 47(8):311–20, 1993.

Miscellaneous opioid peptides, including (but not limited to) adrenal peptide E, alpha casein fragment, beta casomorphin, dermorphin, kyotorphin, metophamide neuropeptide FF (NPFF), melanocyte inhibiting factor, and analogues, agonists and antagonists can be used to treat neurological disorders, alleviating pain, as well as for the treatment of opioid abuse.

Vasotocin and analogues, agonists and antagonists can be used for clinical uses to be determined.

Protein kinase C and inhibitors and analogues, agonists and antagonists can be used to treat cancer, apoptosis, smooth muscle function, and Alzheimer's disease. Examples of these peptides are named and described in Philip, P. A.; Harris, A. L; Potential for protein kinase C inhibitors in cancer therapy. Cancer Treatment & Research 78:3–27, 1995.

Amyloid, amyloid fibrin, fragments and analogues, agonists and antagonists can be used to treat neurodegenerative diseases and diabetes.

Calpain and other calmodulin-inhibitory proteins and analogues, agonists and antagonists can be used to treat neurodegenerative disorders, cerebral ischaemia, cataracts, myocardial ischaemia, muscular dystrophy and platelet aggregation.

Charybdotoxin, Apamin and analogues, agonists and antagonists can be used for treatment of neurodegenerative diseases and pain and cerebral ischemia.

Phospholipase A2 and receptor inhibiting/activating peptides and analogues, agonists and antagonists can be used to treat acute pancreatitis, pancreatic cancer, abdominal trauma, and inflammation, e.g., sepsis, infections, acute pancreatitis, various forms of arthritis, cancer, complications of pregnancy, and postoperative states.

Potassium channel activating and inhibiting proteins and analogues, agonists and antagonists can be used to treat various diseases. Examples of these peptides are described in Edwards, G.; Weston, A. H; Pharmacology of the potassium channel openers. Cardiovascular Drugs & Therapy. 9 Suppl 2:185–93, March 1995.

IgG activators, inhibitors and analogues, agonists and antagonists can be used to treat autoimmune diseases and immune dysfunctions. Examples of these peptides are described in Mouthon, L.; Kaveri, S. V.; Spalter, S. H.; Lacroix-Desmazes, S.; Lefranc, C.; Desai, R.; Kazatchkine, M. D; Mechanisms of action of intravenous immune globulin in immune-mediated diseases. Clinical & Experimental Immunology. 104 Suppl 1:3–9, 1996.

Endotoxin and inhibitors and analogues, agonists and antagonists can be used for decreasing cardiac output, systemic hypotension, decreased blood flow and $O_2$ delivery to tissues, intense pulmonary vasoconstriction and hypertension, bronchoconstriction, increased permeability, pulmonary oedema, ventilation-to-perfusion inequalities, hypoxaemia, and haemoconcentration. Examples of these peptides are named and described in Burrell, R; Human responses to bacterial endotoxin. Circulatory Shock. 43(3) :137–53, July 1994.

The Use of Peptides Containing Non-Natural Amino Acid(s) to Pass a Body Barrier

The invention relates to a method of increasing the ability of a peptide to cross a body barrier of a subject, comprising substituting for at least one natural amino acid in the peptide at least one non-natural amino acid having the formula I–IV, XL, LX, LXX, LXXX, and/or XC whereby the peptide having at least one non-natural amino acid is better able to cross the barrier than a peptide having no non-natural amino acid.

The invention further relates to a method of treating or preventing in a subject a disease treated or prevented by the administration of a peptide that crosses a body barrier, comprising administering to the subject a peptide having, substituted for at least one natural amino acid at least one non-natural amino acid having the formula I–IV, XL, LX, LXX, LXXX, and/or XC whereby the peptide having at least one non-natural amino acid crosses the body barrier in higher amounts than the peptide having no non-natural amino acid.

The invention also relates to a method of treating or preventing in a subject a disease of the brain treated or prevented by the administration of a peptide containing a natural amino acid, comprising administering to the subject the known therapeutic peptide having, substituted for the natural amino acid, at least one non-natural amino acid having the formula I–IV, XL, LX, LXX, LXXX, and/or XC.

The use of peptides as therapeutic agents is limited by their inability to cross body barriers. The phrase "body barrier" is defined herein as a cellular membrane or other structure that functions to prevent free (e.g., diffusional) passage of certain molecules. The substitution of at least one natural amino acid with a compound of the invention facilitates the passage of the resultant peptide through a variety of body barriers. Examples of body barriers include, but are not limited to, the blood brain barrier, a cell membrane, intestinal epithelium, skin cell, or the blood-ocular. In a preferred embodiment, the body barrier is the blood brain barrier. As described above, the non-natural amino acids of the invention are lipophilic than natural amino acids. Therefore, a peptide containing a non-natural amino acid can pass through a body barrier more effectively than a peptide that does not contain a non-natural amino acid.

In one embodiment, a peptide containing arginine and/or lysine is a substituted with one or more compounds of the invention in order to increase the ability of the resultant peptide to cross a body barrier, preferably the blood brain barrier. In another embodiment, when a peptide is used to cross the blood brain barrier, the peptide contains (a) a compound having the formula XL, dashed line c is not present, n is 1, $R_1$l, $R_2$, $R_3$, and $R_{13}$ are hydrogen, and the stereochemistry at $C_\beta$ is S;

(b) a compound having the formula XL, dashed line c is not present, n is 4, $R_1$, $R_2$, and $R_3$ are hydrogen, $R_{13}$ is methyl, and the stereochemistry at $C_\beta$ is S;

(c) a compound having the formula XL, dashed line c is not present, n is 1, $R_1$, $R_2$, and $R_3$ are hydrogen, $R_{13}$ is methyl, and the stereochemistry at $C_\beta$ is S;

(d) a compound having the formula XL, dashed line c is not present, n is 2, $R_1$, $R_2$, and $R_3$ are hydrogen, $R_{13}$ is methyl, and the stereochemistry at $C_\beta$ is S;

(e) a compound having the formula XL, dashed line c is not present, n is 3, $R_1$, $R_2$, and $R_3$ are hydrogen, $R_{13}$ is methyl, and the stereochemistry at $C_\beta$ is S;

(f) a compound having the formula XL, dashed line c is not present, n is 1, $R_1$ and $R_3$ are hydrogen, $R_2$ and $R_{13}$ are methyl, and the stereochemistry at $C_\beta$ is S;

(g) a compound having the formula XL, dashed line c is not present, n is 2, $R_1$ and $R_3$ are hydrogen, $R_2$ and $R_{13}$ are methyl, and the stereochemaistry at $C_\beta$ is S;

(h) a compound having the formula XL, dashed line c is not present, n is 3, $R_1$ and $R_3$ are hydrogen, $R_2$ and $R_{13}$ are methyl, and the stereochemistry at $C_\beta$ is S;

(i) a compound having the formula XL, dashed line c is present, n is 1, $R_1$ and $R_3$ are hydrogen, $R_2$, $R_{13}$, and $R_{15}$ are methyl, the counterion is bromide, and the stereochemistry at $C_\beta$ is S;

(j) a compound having the formula XL, dashed line c is present, n is 2, $R_1$ and $R_3$ are hydrogen, $R_2$, $R_{13}$, and $R_{15}$ are methyl, the counterion is bromide, and the stereochemistry at $C_\beta$ is S;

(k) a compound having the formula XL, dashed line c is present, n is 3, $R_1$ and $R_3$ are hydrogen, $R_2$, $R_{13}$, and $R_{15}$ are methyl, the counterion is bromide, and the stereochemistry at $C_\beta$ is S;

(l) a compound having the formula II, dashed line a is not present, n is 3, X, $R_4$, and $R_5$ are hydrogen, Y is methyl, and the stereochemistry at $C_\beta$ is S;

(m) a compound having the formula II, dashed line a is not present, n is 3, X, $R_4$, and $R_5$ are hydrogen, Y is ethyl, and the stereochemistry at $C_\beta$ is S.

(n) a compound having the formula II, dashed line a is present, n is 3, z is 2, $R_4$, and $R_5$ are hydrogen, and the stereochemistry at $C_\beta$ is S; and/or (o) a compound having the formula III, n is 3, X, $R_6$, $R_7$, and $R_8$ are hydrogen, and the stereochemistry at $C_\beta$ is S.

Compounds a–o can also be used in any of the methods described herein.

Selectivity and Stability of Peptides Containing Non-Natural Amino Acid(s)

The invention relates to a method of increasing the selectivity of a peptide, comprising substituting for at least one natural amino acid at least one non-natural amino acid having the formula I–IV, XL, LX, LXX, LXXX, and/or XC, whereby the peptide having at least one non-natural ammo acid is more selective than the peptide having no non-natural amino acid.

Enhancing the selectivity of a drug to a biological target is of great importance. In one embodiment, the incorporation of one or more non-natural amino acids of the invention into a peptide produces a peptide having higher enzymatic selectivity. In one embodiment, incorporation of one or more non-natural amino acids into inhibitors for the enzyme thrombin results in a substantial increase in the inhibitor's selectivity of the enzyme. It is known in the art that compounds that are selective for thrombin inhibition are of great interest as potential antithrombotics. The non-natural amino acids of the invention, however, can increase the selectivity of a wide variety of peptides depending upon the selection of the non-natural amino acid and the peptide. The increased selectivity of a peptide containing a non-natural amino acid can be attributed in part to the increased hydrophobicity of the non-natural amino acid, which facilitates the passage of the resultant peptide through a body barrier.

In one embodiment, a peptide containing arginine and/or lysine can be substituted with one or more non-natural amino acids of the invention in order to increase the selectivity of the peptide. In another embodiment, any of the non-natural amino acids disclosed herein can be used to increase the selectivity of a peptide.

The invention also relates to a method of increasing the resistance of a peptide to digestion by a peptidase, comprising substituting for at least one natural amino acid in the peptide at least one non-natural amino acid having the formula I–IV, A, LX, LXX, LXXX, and/or XC, whereby the peptide having at least one non-natural amino acid is better able to resist digestion by a peptidase than a peptide having no non-natural amino acid. The non-natural amino acids of the invention impart increased stability to the peptide. When the peptide is further stabilized by the non-natural amino acid, the concentration and half-life of the resultant peptide in the bloodstream also increases.

EXPERIMENTAL

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C and is at room temperature, and pressure is at or near atmospheric.

Example 1

Synthesis of (2R)-7-(N-methylamino)-Z-aminoheptanoic acid (Formula I, wherein n is 4, $R_1$, $R_3$ and $R_{13}$ are hydrogen, $R_2$ is methyl, the compound of formula I is an acid, and the stereochemistry at $C_\beta$ is R) (Scheme F)

Methyl iodide (14.00 g, 98.6 mmoles) was added to a solution of 2-azacyclooctanone (8.00 g, 62.9 mmoles, 2a) (2a is commercially available from Aldrich Chemical Company) in 75 ml dry THF. The resulting solution was cooled in an ice bath Sodium hydride (3.00 g, 75 mmoles) was added slowly and the resulting slurry was warmed to room temperature over an hour and allowed to stir overnight. After this time 100 ml saturated ammonium chloride solution was added, and extracted 3 times with ethyl acetate. The ethyl acetate extracts are dried and evaporated. The crude oil was chromatographed on a 100 gm silica gel (230–400 mesh) column eluting with a 1 to 1 mixture of ethyl acetate and hexane. Fractions containing product are identified by TLC and evaporated yielding (2b) as a pale oil (7.6 g, 53.9 mmoles, 85.7%). The methylated amide (7.00 g, 49.6 mmoles, 2b) in a mixture (ethyl alcohol 35 ml and 1.25 N NaOH 70 ml) was refluxed overnight. The solution was then cooled, neutralized, partially evaporated, and applied to a 50 W Dowex strongly acidic ion exchange column. The amino acid was eluted with 1N ammonium hydroxide and monitored by TLC (aqueous phenolic solution as eluent). The fractions containing the pure amino acid were evaporated under reduced pressure. The product obtained (2c) was an off white solid (7.2 g, 45.3 mmoles, 91.3%). 100 ml $H_2O$ was added slowly over a 1 hour period to a slurry of 1-aminomethyl heptanoic acid (3.18 g, 20 mmoles, 2c) $NaHCO_3$ (2 g, 23.8 mmol), and di-tert-butyl dicarbonate (8.7 g, 40 mmol) in 300 ml dioxane. The solution pH was maintained at 9 during initial period of the reaction by the dropwise addition of 1N NaOH. The reaction was allowed to stir overnight (12 hr). The reaction mixture was concentrated in vacuo and redissolved in 150 ml aqueous NaOH (pH 10.5–11.5). The aqueous solution was placed in a 500 ml separatory funnel and extracted 3 times with ethyl acetate (450 ml total). The aqueous phase was then acidified to pH 1.5 with conc. HCl and immediately extracted 3 times versus ethyl acetate (450 ml total). The organic extracts were combined, dried with $MgSO_4$, filtered, and evaporated with a rotary evaporator. A pale oil was lyophilized to yield (2d) as a pale oil (4.61 g, 17.8 mmoles, 89%). 7-(1,1 dimethylethoxy) amido-methyl-heptanoic acid 2d (2.47 g, 9.5 mmoles) and TEA (1.75 ml, 11.9 mmol) were stirred in 100 ml dry THF and cooled to −78° C. under positive nitrogen pressure. Pivaloyl chloride (1.32 ml, 10.7 mmol) was added via cannula and stirred at 0° C. for 1 hr, then cooled to −78 ° C. In a second reaction vessel, S-4-benzyl-2-oxazolidinone (3.25 g, 18.3 mmol) in 30 ml THF was cooled to −78° C. and kept under positive nitrogen pressure. To this n-butyl lithium 2.5M (7.4 ml, 18.5 mmol) was added slowly via cannula and stirred for 5 minutes. After this time the contents of this vessel were transferred via cannula to the vessel containing the pivaloyl ester. The reaction was then allowed to stir for 1 hr at 0° C. and taken to room temperature after an additional hour of stirring. At this time the THF was removed on a rotary evaporator and the slurry was washed into a separatory funnel with 100 ml each of methylene chloride and phosphate buffer (0.1 M pH 7). After extracting, the methylene chloride phase was saved, and the extraction is repeated two more times. The organic phase was washed with 5% aqueous $NaCO_3$ and half saturated brine, followed by drying with $MgSO_4$. The filtered methylene chloride phase was condensed on a rotary evaporator leaving ~8 g of yellow oil. The crude material was chromatographed on a 350 g silica gel (230–400 mesh) column with a mixture of hexane:ethyl acetate (3:1). A clear oil (2e) was recovered (3.40 g, 8.1 mmoles, 86%) upon evaporation of TLC positive fractions. A solution of (17 ml, 8.5 mmol, 1.1 eq.) bis (trimethylsilyl) amide in 150 ml THF was kept at −78° C. under positive nitrogen pressure. A solution of imide 2e (3.22 g, 7.7 mmoles) in 50 ml dry THF under $N_2$ was precooled to −78° C. and transferred via cannula into the basic solution and stirred for 20 minutes at −78 ° C. At this time a precooled (−78° C.) solution of trisyl azide (6 g, 19.4 mmol, 2.6 eq.) in 40 ml dry THF under $N_2$ pressure is transferred via cannula to the vessel containing the enolate. After 2 minutes the reaction was quenched with the addition of glacial acetic acid (2 ml, 5 eq.) and allowed to stir at room temperature overnight. The reaction mixture was concentrated in vacuo to remove THF. The crude oily yellow solid was partitioned between 100 ml dilute brine and 100 ml methylene chloride. The extraction was repeated twice more and then organic extracts were combined and washed with 5% $NaHCO_3$. The organic solution was dried with $MgSO_4$ and concentrated to give a yellow oil. The crude oil was further purified on a 350 g silica gel (230–400 mesh) column eluting with 1% methanol in methylene chloride. To separate the diastereomers of the stereoselective reaction, a Merck LiChroprep Si 60 (40–63 uM) HPLC column was used eluting with hexane:ethyl acetate (1:1) at a 10 ml per minute flow rate. The desired diastereomer 2f, present as a clear oil was obtained (2.00 g, 4.4 mmoles 56%). A solution of the azido-carboximide 2f (1.58 g, 3.44 mmol) in 52 ml THF and 15 ml $H_2O$ was stirred and cooled to 0° C. The solution was treated with 30% hydrogen peroxide (1.44 ml, 4 equiv.) and then with lithium hydroxide hydrate (286 mg, 6.8 mmol, 2 equiv.) and then stirred at 0° C. for 30 minutes. At that time, 12 ml of sodium sulfite (0.183 g/ml $H_2O$) was added, followed by 36 ml aqueous sodiumbicarbonate (0.5N). The mixture was allowed to warm to room temperature and the residual THF removed on a rotary evaporator. The remaining solution was diluted with 50 ml $H_2O$ and extracted with dichloromethane (4×100 ml). The aqueous layer was acidified to ~pH 1.5 with conc. HCl and extracted with ethyl acetate (4×125 ml). Organic extracts were combined, dried over $MgSO_4$, filtered and concentrated in vacuo to give a pale oil (2g) as product (0.978 g, 3.26 mmoles, 95%). BOC-S Azido Acid (2g) (0.89 g, 2.9 mmoles) was dissolved in anhydrous methanol 25 ml. To this anhydrous 10% palladium on carbon 180 mg was added under ambient $N_2$ atmosphere. This vessel was placed on a Parr reactor under 30 PSI $H_2$ pressure and shaken off and on for 2 days at 5 hour intervals to allow the Parr reactor motor to cool. The solution was filtered and evaporated with a rotary evaporator to give the Boc amino acid as a white powder (0.78 g, 2.8 mmoles, 96%). The amino acid was dissolved in 5 ml $H_2O$ with triethylamine (0.39 ml, 2.8 mmoles). N-(9H-Fluoren-2-ylmethoxy-carbonyloxy) succinimide (1.24 g, 3.7 mmoles) was dissolved in 5 ml warm acetonitrile, and added to the amino acid solution. The pH of the reaction is kept between 8.5 and 9 by the dropwise addition of triethyl amine. After 30 minutes 30 ml $H_2O$ was added and the pH is adjusted to 1.5 and extracted with ethyl acetate twice. The extracts were washed with $H_2O$ and brine, then dried, and evaporated under reduced pressure. The product may be purified by crystallization or chromatographically using silica gel (230–400) mesh eluting with 0.1% acetic acid, and 2% methanol in methylene chloride. The diprotected amino acid (2h) is a yellow oil (0.93 g, 1.9 mmoles, 67%). The Fmoc group was removed from 2h with 5% piperidine quantitatively. The Boc group was removed with aqueous TFA. The unprotected amino acid 2 was purified on a Dowex 50 strongly acidic cation exchangecolumn. Overall yield 20.5%.

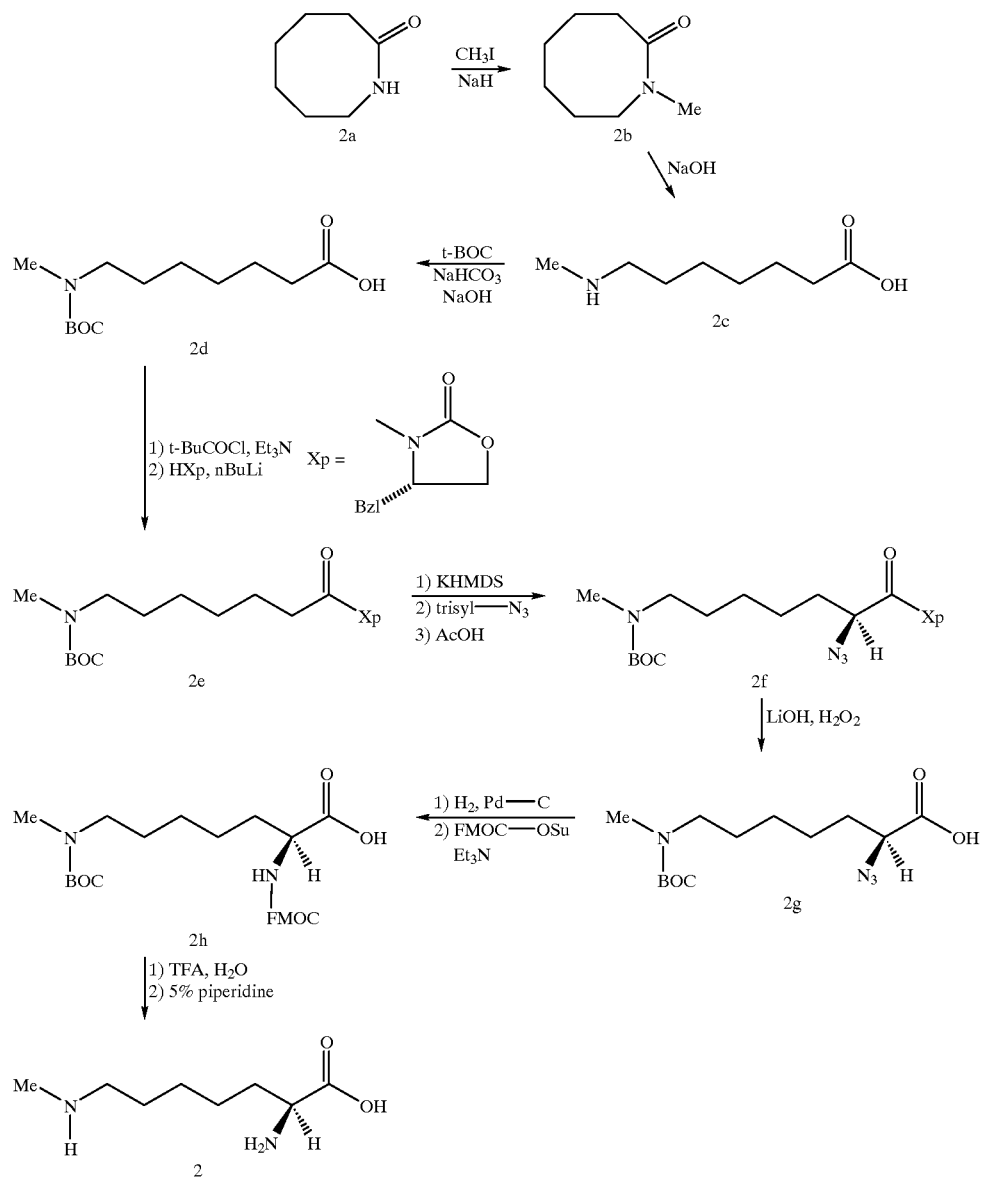

Example 2

Synthesis of (2R,7R)-7-(N-methylamino)-2-aminooctanoic acid (Formula I, wherein n is 4, $R_1$ and $R_2$ are methyl, $R_3$ and $R_{13}$ are hydrogen, the compound of formula I is an acid, the stereochemistry at $C_a$ is $R_{13}$ and the stereochemistry at $C_b$ is R) and (2R,7S)-7-(N-methylamino)-2-aminooctanoic acid (Formula I, wherein n is 4, $R_1$ and $R_2$ are methyl, $R_3$ and $R_{13}$ are hydrogen, the compound of formula I is an acid, the stereochemistry at $C_a$ is S, and the stereochemistry at $C_b$ is R) (Scheme G)

Sodium hydroxide (8 g, 200 mmol) was added to 2-acetylcyclohexanone (25 g, 178 mmol, 3a) (3a is commercially available from Aldrich Chemical Company) in 50 ml $H_2O$. Solution was refluxed for 3 hours and then allowed to cool to room temperature. The resulting yellow solution was extracted with ether (3×50 ml). The aqueous layer was acidified to pH ~1.0 with conc. HCl. Extracted again with ether (3×50 ml) and organic extracts were dried with $MgSO_4$, filtered and concentrated to give the ketoacid 3b ( 22.5 g, 80% yield) as an amber oil. Methylamine hydrochloride (25.5 g, 378 mmol) was dissolved in 150 ml MeOH and the solution was titrated to pH ~6 with dilute HCl. Ketoacid 3b (10 g, 63 mmol) and sodium cyanoborohydride (2.4 g, 38 mmol) were added while stirring. The solution was stirred at room temperature for 72 hours at which time conc. HCl was added to pH 1.5 and the solution stirred for an additional hour. Extracted with ethyl ether (2×150 ml) and the aqueous extract was concentrated to dryness in vacuo. Product was redissolved in a minimum volume of water and purified by ion-exchange chromatography using Dowex 50×8 strongly acidic cation exchanger (350 g) with 1M $NH_4OH$ as eluent. Fractions containing amine were visualized with ninhydrin and combined and concentrated to give 10.07 g (84% yield) of white product 3c as the ammonium salt. To a stirred solution of amine 3c (5 g, 26.3 mmol), $NaHCO_3$ (1.32 g, 15.9 mmol) and di-tert-butyl dicarbonate (7.65 g, 35 mmol) in 200 ml dioxane, 40 ml $H_2O$ was added slowly. The solution was titrated to pH 11 with dilute NaOH and refluxed gently for 12 hours. The clear, pale yellow solution was allowed to cool to room temperature. After concentration to almost dryness on a rotary evaporator, the residue was redissolved in 150 ml aqueous NaOH (pH 11–12) and then extracted with dichloromethane (3×150 ml). The remaining aqueous layer was then acidified to pH 1.5 with conc. HCl and immediately extracted with dicholoromethane (3×150 ml). The organic extracts were combined, dried with $MgSO_4$, filtered and concentrated to give 6.47 g (90% yield) of 3d as a pale yellow oil. A solution of 3d (3.65 g, 13.4 mmol) and triethylamine (2.94 ml, 19.4 mmol) was stirred in 85 ml dry THF and cooled to −78° C. under $N_2$. Pivaloyl chloride (1.70 ml, 19.4 mmol) added via cannula and this solution was stirred for 1 hour at 0° C. and then recooled to −78° C. In another flask a solution of (4S)-(phenylmethyl)-2-oxazolidinone (2.92 g, 16.5 mmol) in 40 ml dry THF was cooled to −78° C. under $N_2$, and 6.6 ml n-butyllithium (2.5M in hexane) added dropwise via cannula. This was allowed to stir for 5 minutes and then added via cannula to the mixed anhydride solution. The mixture was stirred for 20 minutes at −78° C. and 1 hour at 0° C. and then allowed to warm to room temperature. The mixture was partitioned between 200 ml dichloromethane and 200 ml pH 7 phosphate buffer. Organic extracts were combined and washed with 5% aqueous $NaHCO_3$ followed by dilute brine, dried with $MgSO_4$, filtered and concentrated to give a yellow oil. This crude product was chromatographed on 200 g silica gel eluting with 750 ml hexane: ethyl acetate (3:1) followed by hexane:ethyl acetate (1:1) which yielded 4.75 g (82%) of clear oil 3e as final product. A solution of 10.2 ml (1.1 equiv.) of potassium hexamethyldisilazide (0.5M in toulene) stirred in 60 nil dry THF was cooled to −78° C. under $N_2$. A precooled (−78° C.) solution of imide 3e (2.0 g, 4.63 mmol) in 50 ml dry THF under $N_2$ was then added via cannula to the base solution. This mixture was stirred at −78° C. for 20 minutes at which point a precooled solution (−78° C.) of trisyl azide (3.58 g, 11.6 mmol, 2.5 equiv.) in 30 ml dry THF was added via rapid cannulation. The resulting yellow-orange solution was quenched with 0.6 ml (2.2 equiv.) of glacial acetic acid after 1 minute and then warmed immediately to room temperature in a water bath. The mixture was stirred for 2 hours and then partitioned between 200 ml dichloromethane and 200 ml dilute brine. The organic layer was retained and the aqueous layer washed twice more with dichloromethane (2×150 ml). Organic extracts were combined, washed with 5% $NaHCO_3$ (2×200 ml), dried with $MgSO_4$, filtered and concentrated in vacuo to give a crude yellow oil. This product was chromatographed on 200 g silica gel eluting with 500 ml hexane:ethyl acetate (3:1) followed by hexane:ethyl acetate (1:1) and then further purified to separate major and minor diastereomers by HPLC on a Merck LiChroprep Si 60 (40–63 uM) preparative silica column eluting with hexane:ethyl acetate (1:1). Final yield of major diastereomer pair was 1.04 g (51% yield) obtained as a clear oil. Stereoselectivity of the reaction as determined from peak ratios of major and minor products was 98:2. A solution of azidocarboximide 3f (2.79 g, 5.9 mmol) in 110 ml THF and 30 ml $H_2O$ was stirred and cooled to 0° C. The solution was treated with 30% hydrogen peroxide (2.9 ml, 4 equiv.) and then with lithium hydroxide hydrate (562 mg, 13.4 mmol, 2 equiv.) and then stirred at 0° C for 30 minutes. At that time, 20.7 ml of sodium sulfite (0.183 g/ml H2O) was added, followed by 69 ml aqueous sodium bicarbonate (0.5N). The mixture was allowed to cool to room temperature and the residual THE removed on a rotary evaporator. The remaining solution was diluted with 250 ml $H_2O$ and extracted with dichloromethane (4×200 ml). The aqueous layer was acidified to ~pH 1.5 with conc. HCl and extracted with ethyl acetate (4×250 ml). Organic extracts were combined, dried over $MgSO_4$, filtered and concentrated in vacuo to give 1.73 g (94%) of pale oil 3g as final product. Azide 3c (1.73 g, 5.5 mmol) was taken up in 50 ml anhydrous methanol and added to 225 mg 10% palladium/carbon catalyst in a Parr flask. Material was hydrogenated at 30 p.s.i. for about 12 hours in the Parr apparatus. At this time the catalyst was filtered off and the filtrate dried to give a white solid. This material was then protected by dissolving 1.29 g (4.5 mmol) of amino acid in 25 ml $Na_2CO_3$ and 25 ml dioxane and cooling to 0° C. in an ice bath FMOC-Cl (1.16 g, 4.5 mmol) was dissolved in 20 ml dioxane and added slowly to amino acid solution. This mixture was stirred at room temperature for two hours after which time the solution was diluted with 50 ml $H_2O$ and acidified to pH ~1–2 with citric acid. Extracted 3×100 ml ether, dried over $MgSO_4$ and evaporated to dryness to give a yellow syrup. Product can be recrystallized with dichloromethane:petroleum ether or chromatographed on silica gel, eluting with dichloromethane:methanol:acetic acid (2:98:0.5) to give 1.86 g of product 3h as a pale yellow solid (81% yield from 3g). The racemic mixture of product 3h can be separated into the individual enantiomers by HPLC using a Zorbax SIL 4.6 mm×250 mm column eluting with hexane: ethyl acetate, and then deprotected by treatment with conc. HCl followed by 5% piperidine to give the amino acids 3 and 7. Overall yield of products from starting material 3a is 19%.

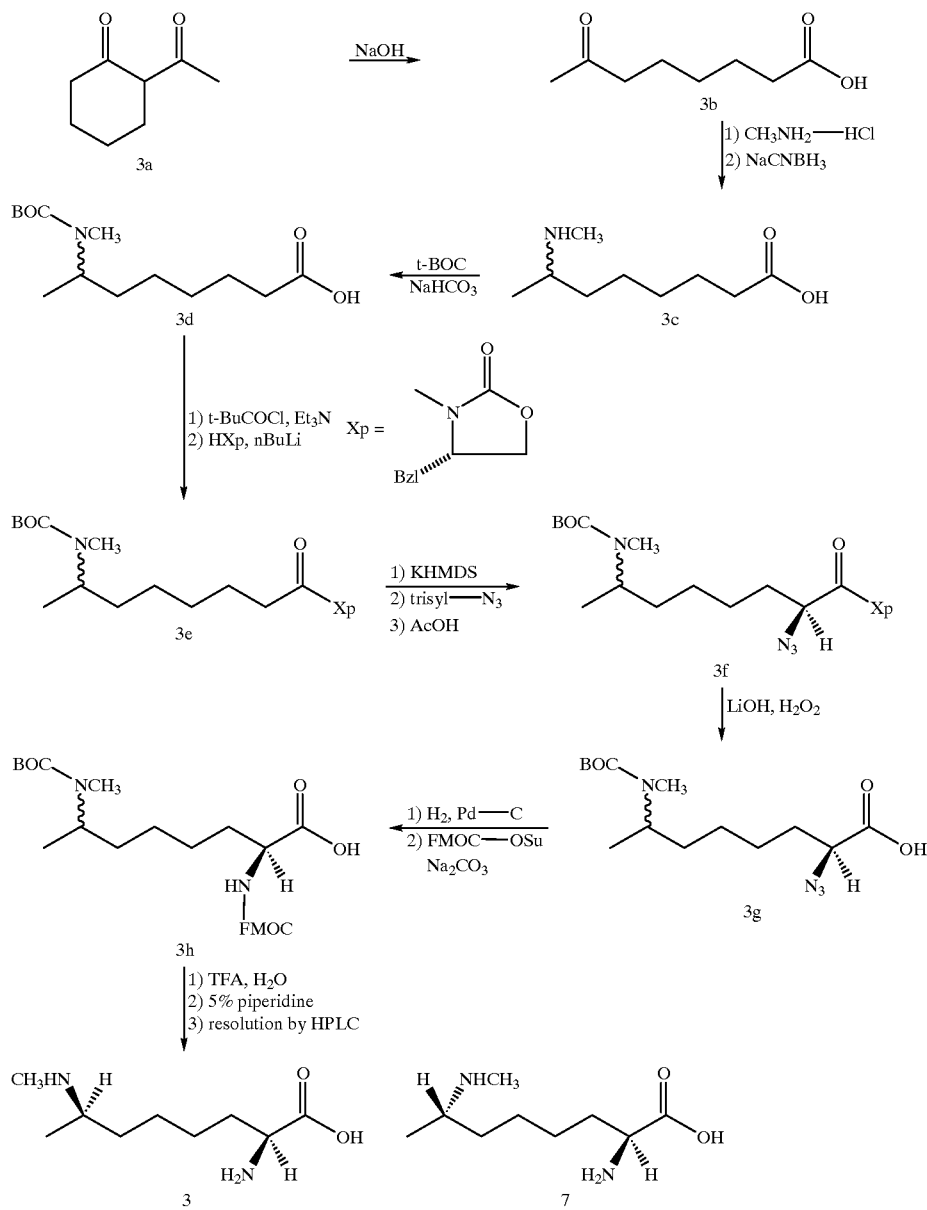

Scheme G

Example 3

Synthesis of (2R)-2-amino-5-(N³-methyl)guanidino valeric acid (Formula II, wherein n is 3, dashed line a is not present, the compound of formula II is an acid, $R_4$ and $R_5$ are hydrogen, X is hydrogen, Y is methyl, and the stereochemistry at $C_b$ is R) (Scheme H)

Methyl iodide (7.1 g, 50 mmol) was added dropwise to a slurry of N-ethyl thiourea (4.5 g, 50 mmol, 13a) (13a is commercially available from Aldrich Chemical Company) in 30 ml of acetone, resulting in a homogenous, pale yellow solution. The solution was refluxed for 10–15 minutes and then filtered hot. The filtrate was brought back to reflux and hexane was added to saturation. White crystals were formed upon cooling to 0° C., and this product was filtered off, washed with cold hexane and dried to give 10.6 g of white solid 13b (86% yield). 1.69 g (10 mmol) of L-ornithine hydrochloride and 2.46 g (10 mmol) of N-Ethyl-S-Methyl-isothiouronium iodide, 13b were dissolved in 10 ml 2N NaOH and stirred at room temperature for 9 days. At this time solution was brought to neutral pH with concentrated HCl and chromatographed on 500 g Dowex 50×8 strongly-acidic cation exchange resin. The column was washed with 500 ml water and product was eluted with 1M ammonium hydroxide. Fractions were monitored by TLC with phenol:water (75:25) eluent and visualized by ninhydrin spray. Fractions containing product were pooled and dried on a rotary evaporator to give 1.11 g of amino acid 13 as the ammonium salt. Ion-exchange chromatography is not completely efficient in separating product from starting material but mixed fractions can be pooled and saved for another round of chromatography. Yield of pure product after one round of chromatography is 51%.

Scheme H

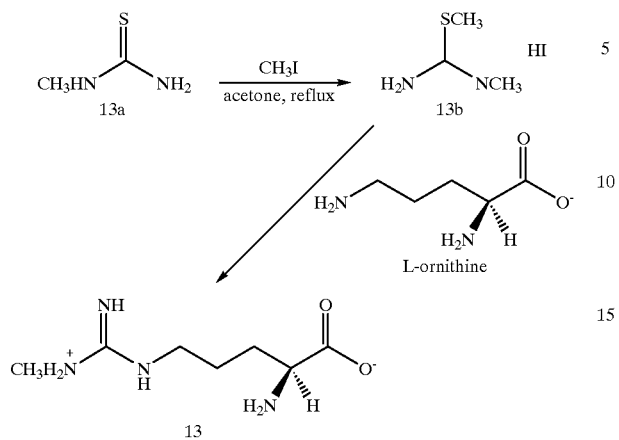

Example 4
Synthesis of (2S)-2-amino-5-(N-methylaminoimino)-valeric acid (Formula III, wherein n is 3, z is 2, $R_6$, $R_7$ and $R_8$ are hydrogen, the compound of formula III is an acid, and the stereochemistry at $C_b$ is R) (Scheme I)

Methyl iodide (1.22 g, 8.6 mmoles) was dropwise added to a slurry of 3,4,5,6-tetrahydro-2-pyrimidinethiol (1.00 g, 8.6 mmoles, 21a) (21a is commercially available from Aldrich Chemical Company) in 50 ml of acetone. The reaction mixture was refluxed for 10 minutes and 2–5 mL of ethanol was added to dissolve the precipitate formed. The clear solution was saturated with hexane (about 25 mL) while hot. White crystals formed upon cooling at 0° C. The product was filtered off, washed with cold hexane (10 mL) and dried, yielding 1.5 g of S-methylthiopseudouronium iodide 21b (5.8 mmoles, 67.5%). About 0.90 g (5.4 mmoles) ornithine 21c was dissolved in 50 mL 1N NaOH solution and 1.4 g (5.4 mmoles) of intermediate 21b was added with stirring. The mixture was refluxed for 4 hours, then it was cooled to room temperature and the pH was brought to 4 with HCl. The solution was applied to a Dowex 50W ion exchange column in the H⁺ form. The column was washed with water until the eluate was neutral then washed with 0.2 N ammonium hydroxide. The amino acid was eluted with 1.5 N ammonium hydroxide and monitored by TLC (aqueous phenolic solution as eluent). The fractions containing the pure amino acid were evaporated under reduced pressure. The product obtained (21) was an off-white solid (0.55 g, 2.6 mmoles, 37.6%). Overall average yield was about 25%.

Scheme I

Example 5
Synthesis of (2R)-2-amino-5-(N-(2-imidzolidine))-valeric acid (Formula IV, wherein n is 3, $R_9$ and $R_{12}$ are hydrogen, $R_{10}$ and $R_{11}$ are methyl, the compound of formula IV is an acid, and the stereochemistry at $C_b$ is R) (Scheme J)

Na-tBOC-L-ornithine (1.00 g, 4.31 mmoles) is dissolved in 10 ml 10% $Na_2CO_3$ and 20 ml THF. Methyl iodide (0.63 g, 4.5 mmoles) is dropwise added and the reaction mixture is refluxed for 30 min and then evaporated to dryness. Ne-methyl-Na-t-BOC-L-ornithine (30a) was purified via silica gel chromatography as a flaky white solid (0.46 g, 1.87 mmoles, 43.4%). Methyl acetimidate (0.88 g, 8.0 mmoles) is added to intermediate 30a (100 g, 4.07 mmoles) in 30 ml MeOH (pH 10) and stirred at 70° C. for 4 hr. The reaction mixture was evaporated to dryness and subjected to silica gel chromatography where intermediate 30b was isolated as an off-white powder (0.73 g, 2.53 mmoles, 62%). t-BOC deprotection of 30b (1.00 g, 3.47 mmoles) was done with 95% TFA in MeOH for 1 hr and reprotected with FMOC-Cl (0.93 g, 3.6 mmoles) in 25 ml 10% $Na_2CO_3$ and 25 ml dioxane (pH 10) at 0° C. for 45 min. The product obtained (30) is a yellow solid (0.98 g, 2.4 mmoles, 67%). Overall synthetic yield nears 18%.

Scheme J

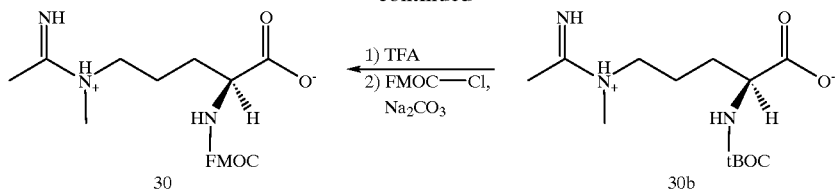

Example 6
(D)-Phe-Pro-7-Ala peptide as an inhibitor of thrombin

Approximately one third of premature deaths in the United States today result from thrombotic disorders. The serine protease thrombin is involved at all levels of thrombosis, hence, inhibiting this enzyme provides the most direct way to control these disorders. Current antithrombotic therapies are considered inadequate as the agents employed have a variable window of therapeutic action and are not orally bioavailable due to their size and hydrophilicity. Various tripeptide analogues of the general formula (D)-Phe-Pro-Arg-X (where the X group is variable or optional), are potent thrombin inhibitors that exhibit significant oral bioavailabillity. Development of better thrombin-binding inhibitors based on this sequence is thus of considerable interest.

A (D)-Phe-Pro-Arg-Ala analogue containing non-natural amino acid (7) (as the racemic mixture in the side chain) in place of Arg was synthesized and compared to (D)-Phe-Pro-Arg-Ala as a competitive inhibitor of thrombin in vitro. The molecule referred to as 7 is Formula I, $R_1=CM_3$, $R_2=H$, $R_3=H$, $R_{13}=H$ and N=4. The stereochemistry at $C_2$ is racemic (equal D- and L- forms present).

Peptides were incubated individually at 20 μM concentrations with 0.01 units of human thrombin (Sigma) and saturating concentrations of the chromogenic substrate (D)-Phe-Pip-Arg-p-NA at pH 7.5 and 25° C. in 0.1 M phosphate buffer containing 0.2 M NaCl and 0.5% PEG (5c). Initial rates were determined by monitoring formation of p-NA at 405 nm in the absence and presence of the indicated peptides to determine % inhibition. Standard errors were <5%.

As seen in Table 1, the tetrapeptide containing non-natural amino acid 7 is about a 25% better competitive inhibitor than the parent peptide. This demonstrates that a non-natural Arg analogue, when substituted for Arg in a biologically active peptide, can improve the binding characteristics of the peptide. It is likely that either the (R) or (S) epimer in the side chain of amino acid 7 is the active species, which would make the tetrapeptide containing 7 with the desired stereochemistry even more active.

TABLE 1

Thrombin Inhibitors

| Inhibitor | % Inhibition |
|---|---|
| (D)-Phe-Pro-Arg-Ala | 65 |
| (D)-Phe-Pro-7-Ala | 82 |

Example 7
Enhancement of BBB Access of a Neuroactive Peptide

The tridecapeptide neurotensin (NT) has a multifaceted, although incompletely understood, role in brain biochemistry, largely due to the existence of multiple NT receptors (NTR-1, -2, and -3) with overlapping activities and a lack of NTR-specific agonists/antagonists. NT may function as an endogenous neuroleptic as low central nervous system (CNS) levels have been implicated in the pathology of schizophrenia. Stable, receptor-specific agonists of NT that cross the blood brain barrier (BBB) could be used to elucidate the molecular mechanisms of NT in brain functioning and would have significant potential for development as novel antipsychotic drugs. NT(8–13), $Arg^{(8)}$-$Arg^{(9)}$-$Pro^{(10)}$-$Tyr^{(11)}$-$Ile^{(12)}$-$Leu^{(13)}$-COOH, is the minimal structure that produces biological effects comparable to NT. It does not cross the blood brain barrier, but two derivative, NT-1 and NT-66L, cross to a small extent (less than 0.1%).

Several NT(8–13) derivatives were evaluated for ability to elicit hypothermia in rats when injected intracranially (I.C.) to demonstrate the inherent central activity of the peptides) and intravenously (I.V.) to evaluate potential for crossing the BBB). Peptides 36, 39, 42, and 45 are NT(8–13) with non-natural amino acids 32–35 (Scheme L), respectively, were substituted for the $Arg^{(8)}$ residue. While no activity was observed with NT(8–13) injected I.V, all four novel peptides that were tested demonstrated significant uptake into brain, as estimated by their ability to cause hypothermia (FIG. 1A) which is an indication of NT receptor binding. Of these, peptide 36 had roughly 28% uptake into brain after a single 0.2-mg I.V. dose (as estimated by potency ratios; FIG. 1B), indicating at least a 300-fold improvement upon the previously evaluated peptides NT-1 and NT66L.

Scheme L

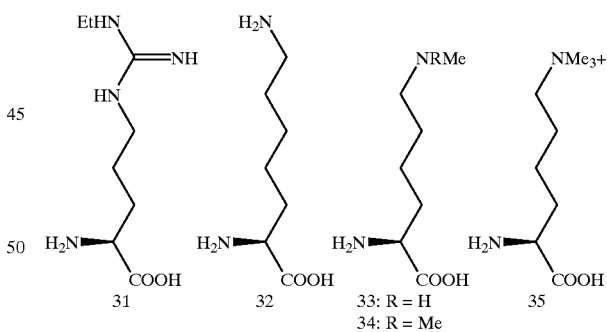

Example 8
Demonstration of the Potential for Selectivity Enhancement

Thrombin is a major control point of the blood coagulation cascade, and inhibitors are of interest to combat thrombotic diseases. Thrombin inhibitors must be selective so as not to affect other blood coagulation enzymes, or proteases in general (e.g., trypsin). Derivatives of arginine (Arg) having large, lipophilic groups (DNS, Pip) are thrombin inhibitors, however, their clinical utility has been compromised due to lack of selectivity. N(γ)ethyl-Arg (31) (Scheme L) was prepared and compared with arginine as thrombin and trypsin inhibitors. Both are excellent inhibitors of thrombin (Table 2). However, the addition of the ethyl group in 31 converted arginine from a good to poor inhibitor of trypsin, and raised the selectivity ratio for thrombin [$K_i$ (Thrombin/Trypsin)] a minimum of 60-fold (the compound does not inhibit trypsin at its limit of solubility in water). Compound 31 was also more lipophilic based on RP-HPLC, which indicates the potential for better barrier access. Thus, the incorporation of a compound of the invention can lead to dramatic selectivity increases while increasing lipophilicity.

TABLE 2

Arginine and compound 31 as thrombin and trypsin inhibitors.

| Compound[1] | Thrombin $K_i$2 (nM) | Trypsin $K_i$ (nM) | $K_i$ (Thrombin/ Trypsin) | RP-HPLC Retention Time (min) |
|---|---|---|---|---|
| Arg | 83 ± 24 | 2.34 ± 0.15 | 28.1 | 20.9 ± 0.02 |
| 31 | 190 ± 66 | >3200 | >1700 | 23.1 ± 0.01 |

[1]As the N-α-DNS, —COO-Pip derivatives.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A non-natural amino acid compound of the formula XL:

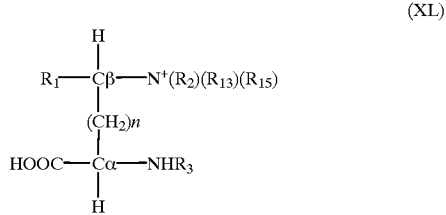

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

wherein the compound comprises a counterion.

2. The compound of claim 1, wherein (a) n is 1, $R_1$ and $R_3$ are hydrogen, $R_2$, $R_{13}$, and $R_{15}$ are methyl, the counterion is bromide, and the stereochemistry at $C_\beta$ is S;

(b) n is 2, $R_1$ and $R_3$ are hydrogen, $R_2$, $R_{13}$, and $R_{15}$ are methyl, the counterion is bromide, and the stereochemistry at $C_\beta$ is S; and p1 (c) n is 3, $R_1$ and $R_3$ are hydrogen, $R_2$, $R_{13}$, and $R_{15}$ are methyl, the counterion is bromide, and the stereochemistry at $C_\beta$ is S.

3. A peptide comprising the non-natural amino acid of claim 1.

4. A method for screening a peptide containing a non-natural amino acid compound for an activity, comprising the steps of:

a) measuring a known activity or pharmacological activity of a peptide having a known amino acid sequence comprising at least one natural amino acid; and b) measuring the same activity or pharmacological activity of a peptide having the same amino acid as in step (a), with the exception that at least one natural amino acid is substituted with a non-natural amino acid having the formula XL:

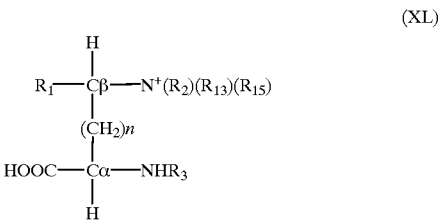

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

wherein the compound comprises a counterion.

5. The method of claim 4, wherein the compound is substituted for the comparable at least one natural amino acid of lysine and/or arginine.

6. The method of claim 4, wherein the pharmacological activity is half-life, solubility, or stability.

7. The method of claim 4, wherein the pharmacological activity is body barrier passage.

8. The method of claim 4, wherein the pharmacological activity is selectivity.

9. A method of treating or preventing in a subject a disease treated or prevented by the administration of a peptide containing a natural amino acid, comprising administering to the subject the known therapeutic peptide having, substituted for the natural amino acid, at least one non-natural amino acid having the formula XL:

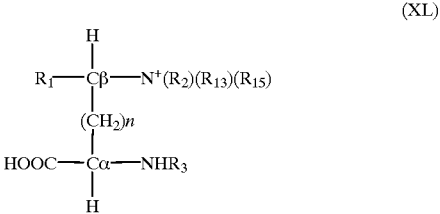

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

wherein the compound comprises a counterion.

10. The method of claim 9, wherein the natural amino acid is lysine and/or arginine.

11. A method of increasing the ability of a peptide to cross a body barrier of a subject, comprising substituting for at least one natural amino acid in the peptide at least one non-natural amino acid compound having the formula XL:

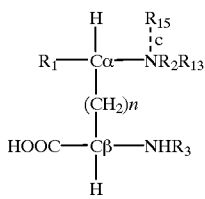

(XL)

wherein
  n is an integer of from 1 to 4;
  $R_1$, $R_2$, $R_3$, $R_{13}$, and $R_{15}$ are, independently, hydrogen or lower branched or straight chain alkyl, alkenyl or alkynyl of $C_1$–$C_5$; and
  $C_\alpha$ and $C_\beta$ are carbon atoms and the stereochemistry at $C_\alpha$ and $C_\beta$ is, independently, either R or S;
  or the ester or salt thereof,
  wherein when dashed line c is present, then $R_{15}$ is present, and when dashed line c is not present, then $R_{15}$ is not present; wherein when dashed line c is present, the compound is a salt comprising a counterion;
  when dashed line c is not present, and $R_1$, $R_2$, $R_3$ and $R_{13}$ are all hydrogen, then n is not 2 or 3;
  when dashed line c is not present, n is 2 or 3, $R_1$ and $R_{13}$ are hydrogen, and $R_2$ and $R_3$ are independently hydrogen or methyl with at least one of $R_2$ and $R_3$ being methyl, then the stereochemistry at $C_\beta$ is not S, and
  when dashed line c is not present, n is 4, and $R_1$, $R_2$, $R_3$ and $R_{13}$ are all hydrogen, then the stereochemistry at $C_\beta$ is not R.

12. The method of claim 11, wherein the barrier comprises the blood brain barrier, a cell membrane, intestinal epithelium, skin, or blood-ocular.

13. The, method of claim 11, wherein the barrier is the blood brain barrier.

14. The method of claim 11, wherein the natural amino acid comprises arginine and/or lysine.

15. The method of claim 11, wherein the compound comprises:
  (a) a compound having the formula XI, dashed line c is not present, n is 1, $R_1$, $R_2$, $R_3$, and $R_{13}$ are hydrogen, and the stereochemistry at $C_\beta$ is S;
  (b) a compound having the formula XL, dashed line c is not present, n is 4, $R_1$, $R_2$, and $R_3$ are hydrogen, $R_{13}$ is methyl, and the stereochemistry at $C_\beta$ is S;
  (c) a compound having the formula XL, dashed line c is not present, n is 1, $R_1$, $R_2$, and $R_3$ are hydrogen, $R_{13}$ is methyl, and the stereochemistry at $C_\beta$ is S;
  (d) a compound having the formula XL, dashed line c is not present, n is 2, $R_1$, $R_2$, and $R_3$ are hydrogen, $R_{13}$ is methyl, and the stereochemistry at $C_\beta$ is S;
  (e) a compound having the formula XL, dashed line c is not present, n is 3, $R_1$, $R_2$, and $R_3$ are hydrogen, $R_{13}$ is methyl, and the stereochemistry at $C_\beta$ is S;
  (f) a compound having the formula XL, dashed line c is not present, n is 1, $R_1$ and $R_3$ are hydrogen, $R_2$ and $R_{13}$ are methyl, and the stereochemistry at $C_\beta$ is S;
  (g) a compound having the formula XL, dashed line c is not present, n is 2, $R_1$ and $R_3$ are hydrogen, $R_2$ and $R_{13}$ are methyl, and the stereochemistry at $C_\beta$ is S;
  (h) a compound having the formula XL, dashed line c is not present, n is 3, $R_1$ and $R_3$ are hydrogen, $R_2$ and $R_{13}$ are methyl, and the stereochemistry at $C_\beta$ is S;
  (i) a compound having the formula XL, dashed line c is present, n is 1, $R_1$ and $R_3$ are hydrogen, $R_2$, $R_{13}$, and R are methyl, the counterion is bromide, and the stereochemistry at $C_\beta$ is S;
  (j) a compound having the formula XL, dashed line c is present, n is 2, $R_1$ and $R_3$ are hydrogen, $R_2$, $R_{13}$ and $R_{15}$ are methyl, the counterion is bromide, and the stereochemistry at $C_\beta$ is S;
  (k) a compound having the formula XL, dashed line c is present, n is 3, $R_1$ and $R_3$ are hydrogen, $R_2$, $R_{13}$, and $R_{15}$ are methyl, the counterion is bromide, and the stereochemistry at $C_\beta$ is S;
  (l) a compound having the formula II, dashed line a is not present, n is 3, X, $R_4$, and $R_5$ are hydrogen, Y is methyl, and the stereochemistry at $C_\beta$ is S;
  (m) a compound having the formula II, dashed line a is not present, n is 3, X, $R_4$, and $R_5$ are hydrogen, Y is ethyl, and the stereochemistry at $C_\beta$ is S;
  (n) a compound having the formula II, dashed line a is present, n is 3, z is 2, $R_4$, and $R_5$ are hydrogen, and the stereochemistry at $C_\beta$ is S; and
  (o) a compound having the formula III, n is 3, X, $R_6$, $R_7$, and $R_8$ are hydrogen, and the stereochemistry at $C_\beta$ is S.

16. A method of increasing the selectivity of a peptide, comprising substituting for at least one natural amino acid at least one non-natural amino acid having the formula XL:

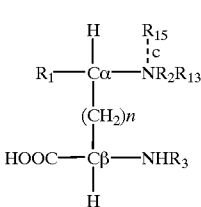

(XL)

wherein
  n is an integer of from 1 to 4;
  $R_1$, $R_2$, $R_3$, $R_{13}$, and $R_{15}$ are, independently, hydrogen or lower branched or straight chain alkyl, alkenyl or alkynyl of $C_1$–$C_5$; and
  $C_\alpha$ and $C_\beta$ are carbon atoms and the stereochemistry at $C_\alpha$ and $C_\beta$ is, independently, either R or S;
  or the ester or salt thereof,
  wherein when dashed line c is present, then $R_{15}$ is present, and when dashed line c is not present, then $R_{15}$ is not present; wherein when dashed line c is present, the compound is a salt comprising a counterion;
  when dashed line c is not present, and $R_1$, $R_2$, $R_3$ and $R_{13}$ are all hydrogen, then n is not 2 or 3;
  when dashed line c is not present, n is 2 or 3, $R_1$ and $R_{13}$ are hydrogen, and $R_2$ and $R_3$ are independently hydrogen or methyl with at least one of $R_2$ and $R_3$ being methyl, then the stereochemistry at $C_\beta$ is not S, and
  when dashed line c is not present, n is 4, and $R_1$, $R_2$, $R_3$ and $R_{13}$ are all hydrogen, then the stereochemistry at $C_\beta$ is not R,
whereby the peptide having at least one non-natural amino acid is more selective than the peptide having no non-natural amino acid.

17. The method of claim 16, wherein the natural amino acid comprises arginine and/or lysine.

18. A method of increasing the resistance of a peptide to digestion by a peptidase, comprising substituting for at least one natural amino acid in the peptide at least one non-natural amino acid having the formula XL:

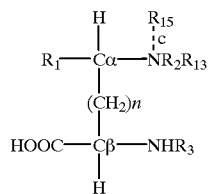

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

or the ester or salt thereof, wherein when dashed line c is present, then $R_{15}$ is present, and when dashed line c is not present, then $R_{15}$ is not present; wherein when dashed line c is present, the compound is a salt comprising a counterion;

when dashed line c is not present, and $R_1$, $R_2$, $R_{13}$ and $R_{13}$ are all hydrogen, then n is not 2 or 3;

when dashed line c is not present, n is 2 or 3, $R_1$ and $R_{13}$ are hydrogen, and $R_2$ and $R_3$ are independently hydrogen or methyl with at least one of $R_2$ and $R_3$ being methyl, then the stereochemistry at $C_\beta$ is not S, and when dashed line c is not present, n is 4, and $R_1$, $R_2$, $R_3$ and $R_{13}$ are all hydrogen, then the stereochemistry at $C_\beta$ is not R, whereby the peptide having at least one non-natural amino acid is better able to resist digestion by a peptidase than a peptide having no non-natural amino acid.

19. The method of claim 18, wherein the natural amino acid comprises arginine and/or lysine.

20. A method of treating or preventing in a subject a disease treated or prevented by the administration of a peptide that crosses a body barrier, comprising administering to the subject a peptide having, substituted for at least one natural amino acid at least one non-natural amino acid having the formula XL:

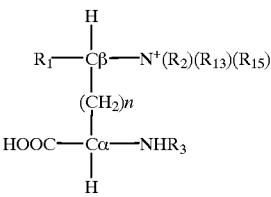

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

wherein the compound comprises a counterion, whereby the peptide having at least one non-natural amino acid crosses the body barrier in higher amounts than the peptide having no non-natural amino acid.

21. A method of treating or preventing in a subject a disease of the brain treated or prevented by the administration of a peptide containing a natural amino acid, comprising administering to the subject the known therapeutic peptide having, substituted for the natural amino acid, at least one non-natural amino acid having the formula XL:

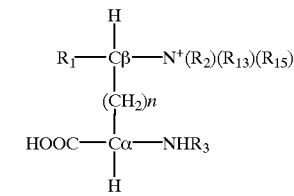

(XL)

wherein n is an integer of from 1 to 4;

$R_1$, $R_2$, $R_3$, $R_{13}$, and $R_{15}$ are, independently, hydrogen or lower branched or straight chain alkyl, alkenyl or alkynyl of $C_1$–$C_5$; and $C_\alpha$ and $C_\beta$ are carbon atoms and the stereochemistry at $C_\alpha$ and $C_\beta$ is, independently, either R or S;

wherein the compound comprises a counterion.

* * * * *